United States Patent
Myhren et al.

(10) Patent No.: US 9,867,856 B2
(45) Date of Patent: *Jan. 16, 2018

(54) PHOSPHOLIPID COMPOSITIONS AND THEIR PREPARATION

(71) Applicant: Aker BioMarine Antarctic AS, Stamsund (NO)

(72) Inventors: Finn Myhren, Oslo (NO); Nils Hoem, Oslo (NO); Håvard Thøgersen, Oslo (NO)

(73) Assignee: AKER BIOMARINE ANTARCTIC AS, Stamsund (NO)

( * ) Notice: Subject to any disclaimer, the term of this patent is extended or adjusted under 35 U.S.C. 154(b) by 0 days.

This patent is subject to a terminal disclaimer.

(21) Appl. No.: 15/110,554

(22) PCT Filed: Jan. 9, 2015

(86) PCT No.: PCT/EP2015/050370
§ 371 (c)(1),
(2) Date: Jul. 8, 2016

(87) PCT Pub. No.: WO2015/104401
PCT Pub. Date: Jul. 16, 2015

(65) Prior Publication Data
US 2016/0339062 A1    Nov. 24, 2016

(30) Foreign Application Priority Data

Jan. 10, 2014  (GB) .................................. 1400431.1

(51) Int. Cl.
| A61K 35/612 | (2015.01) |
| A61K 31/683 | (2006.01) |
| A61K 31/685 | (2006.01) |
| A61K 31/122 | (2006.01) |
| A61K 31/20 | (2006.01) |
| A61K 31/201 | (2006.01) |
| A61K 31/575 | (2006.01) |

(52) U.S. Cl.
CPC .......... *A61K 35/612* (2013.01); *A61K 31/122* (2013.01); *A61K 31/20* (2013.01); *A61K 31/201* (2013.01); *A61K 31/575* (2013.01); *A61K 31/683* (2013.01); *A61K 31/685* (2013.01)

(58) Field of Classification Search
CPC .... A61K 31/685; A61K 31/201; A61K 31/20; A61K 31/575; A61K 31/122; A61K 35/612
See application file for complete search history.

(56) References Cited

U.S. PATENT DOCUMENTS

| 2,652,235 A | 9/1953 | Samuelsen |
| 4,036,993 A | 7/1977 | Ikeda |
| 4,038,722 A | 8/1977 | Terase et al. |
| 4,119,619 A | 10/1978 | Rogozhin et al. |
| 4,133,077 A | 1/1979 | Jasniewicz |
| 4,251,557 A | 2/1981 | Shimose et al. |
| 4,505,936 A | 3/1985 | Meyers et al. |
| 4,714,571 A | 12/1987 | Kearns et al. |
| 4,749,522 A | 6/1988 | Kamarei |
| 4,814,111 A | 3/1989 | Kearns et al. |
| 5,006,281 A | 4/1991 | Rubin et al. |
| 5,266,564 A | 11/1993 | Modolell |
| 5,434,183 A | 7/1995 | Larsson-Backstrom |
| 6,214,396 B1 | 4/2001 | Barrier |
| 6,346,276 B1 | 2/2002 | Tanouchi et al. |
| 6,537,787 B1 | 3/2003 | Breton |
| 6,800,299 B1 | 10/2004 | Beaudoin |
| 7,488,503 B1 | 2/2009 | Porzio et al. |
| 7,666,447 B2 | 2/2010 | Rockway |
| 8,030,348 B2 | 10/2011 | Sampalis |
| 8,057,825 B2 | 11/2011 | Sampalis |
| 8,278,351 B2 | 10/2012 | Sampalis |
| 8,372,812 B2 | 2/2013 | Tilseth et al. |
| 8,383,675 B2 | 2/2013 | Sampalis |
| 8,697,138 B2 | 4/2014 | Bruheim et al. |
| 9,028,877 B2 | 5/2015 | Bruheim et al. |
| 9,034,388 B2 | 5/2015 | Bruheim et al. |
| 9,072,752 B1 | 7/2015 | Bruheim et al. |
| 9,078,905 B2 | 7/2015 | Bruheim et al. |
| 9,119,864 B2 | 9/2015 | Bruheim et al. |
| 9,295,683 B2 * | 3/2016 | Berge ..................... A23L 33/00 |
| 2002/0076468 A1 | 6/2002 | Saxby |

(Continued)

FOREIGN PATENT DOCUMENTS

| AU | 2002322233 | 2/2003 |
| BR | 8701265 | 3/1987 |

(Continued)

OTHER PUBLICATIONS

Takahashi et al., Prediction of Relative Retention Value of the Individual Molecular Species of Diacyl Glycerolipid on High Performance Liquid Chromatography, Bull. Fac. Fish. Hokkaido Univ. 38(4), 398-404. 1987.

Tanaka, Biosynthesis of 1,2-dieicosapentaenoyl-sn-glycero-3-phosphocholine in Caenorhabditis elegans, Eur. J. Biochem. 263, 189±194 (1999).

Tocher, Chapter 6, Glycerophospholipid metabolism, Biochemistry and molecular biology of fishes, vol. 4, Hochachka and Mommsen (eds.)(1995).

Watanabe et al., Effective Components in Cuttlefish Meal and Raw Krill for Improvement of Quality of Red Seabream Pagrus major Eggs, Nippon Suisan Gakkaishi 57(4):681-694 (1991)("Watanabe").

WHO News and Activities, Bulletin of the World Health Organization, 73(4), pp. 547-551 (1995) ("WHO Bulletin").

(Continued)

*Primary Examiner* — Shirley V Gembeh
(74) *Attorney, Agent, or Firm* — Casimir Jones, S.C.

(57) ABSTRACT

The invention provides improved processes for extracting and preparing polar lipids (in particular, desirable phospholipids) from krill and other biological sources. The inventors have discovered processes through which it is possible to extract phospholipids to give high phospholipid content and a reduction of undesired components.

7 Claims, No Drawings

(56) References Cited

U.S. PATENT DOCUMENTS

| | | |
|---|---|---|
| 2003/0044495 A1 | 3/2003 | Kagan |
| 2003/0113432 A1 | 6/2003 | Yoshitomi |
| 2004/0241249 A1 | 12/2004 | Sampalis |
| 2005/0003073 A1 | 1/2005 | Pivovarov et al. |
| 2006/0078625 A1 | 4/2006 | Rockway |
| 2006/0193962 A1 | 8/2006 | Kamiya et al. |
| 2008/0166419 A1 | 7/2008 | Sones |
| 2008/0166420 A1 | 7/2008 | Sones |
| 2009/0061067 A1 | 3/2009 | Tilseth et al. |
| 2010/0143571 A1 | 6/2010 | Breivik |
| 2010/0160659 A1 | 6/2010 | Catchpole |
| 2010/0226977 A1 | 9/2010 | Tilseth et al. |
| 2011/0130458 A1 | 6/2011 | Breivik |
| 2014/0005421 A1 | 1/2014 | Bruheim et al. |
| 2014/0010888 A1 | 1/2014 | Bruheim et al. |
| 2014/0080791 A1 | 3/2014 | Berge et al. |
| 2014/0088043 A1 | 3/2014 | Hoem et al. |
| 2014/0088047 A1 | 3/2014 | Hoem et al. |
| 2014/0107072 A1 | 4/2014 | Tilseth et al. |
| 2014/0274968 A1 | 9/2014 | Berge et al. |
| 2014/0363517 A1 | 12/2014 | Bruheim et al. |
| 2014/0370115 A1 | 12/2014 | Hoem et al. |
| 2015/0030718 A1 | 1/2015 | Saebo |
| 2015/0050403 A1 | 2/2015 | Tilseth et al. |
| 2015/0164841 A1 | 6/2015 | Hoem et al. |

FOREIGN PATENT DOCUMENTS

| | | |
|---|---|---|
| CA | 1098900 | 4/1981 |
| CA | 2251265 | 4/2000 |
| CL | 40348 | 7/1997 |
| CN | 102746941 | 1/2014 |
| EP | 0609078 | 8/1994 |
| EP | 0670306 | 6/1995 |
| EP | 1127497 | 8/2001 |
| EP | 1392623 | 3/2004 |
| EP | 1406641 | 4/2004 |
| EP | 1631280 | 4/2004 |
| EP | 1542670 | 6/2005 |
| EP | 0973532 | 9/2005 |
| EP | 1689413 | 8/2006 |
| EP | 1660071 | 1/2007 |
| EP | 1743531 | 1/2007 |
| EP | 1123368 | 4/2008 |
| EP | 1419768 | 1/2009 |
| EP | 1292294 | 3/2009 |
| EP | 1706106 | 7/2009 |
| EP | 1385500 | 7/2010 |
| GB | 2097014 | 10/1982 |
| GB | 921537 | 6/1999 |
| JP | S51-125774 | 11/1976 |
| JP | S52-114046 | 9/1977 |
| JP | 60-153779 | 8/1985 |
| JP | 61281159 | 12/1986 |
| JP | 02049091 | 2/1990 |
| JP | 2215351 | 8/1990 |
| JP | 4012665 | 1/1992 |
| JP | 2963152 | 2/1992 |
| JP | 04057853 | 2/1992 |
| JP | 3081692 | 7/1994 |
| JP | 2524217 | 8/1996 |
| JP | H08-231391 | 8/1996 |
| JP | 3344887 | 7/1997 |
| JP | 3611222 | 8/1997 |
| JP | 2909508 | 6/1999 |
| JP | 2001-158736 | 6/2001 |
| JP | 2003-003192 | 1/2003 |
| JP | 2003-048831 | 2/2003 |
| JP | 2003-146883 | 5/2003 |
| JP | 3467794 | 9/2003 |
| JP | 2003-530448 | 10/2003 |
| JP | 3486778 | 10/2003 |
| JP | 2004-534800 | 11/2004 |
| JP | 3678317 | 5/2005 |
| JP | 2005-245379 | 9/2005 |
| JP | 2006-069948 | 3/2006 |
| JP | 2006-083136 | 3/2006 |
| JP | 2006-290784 | 10/2006 |
| JP | 2006-316073 | 11/2006 |
| JP | 2006-328014 | 12/2006 |
| JP | 2007-126455 | 5/2007 |
| JP | 2007-246404 | 9/2007 |
| SU | 220741 | 1/1971 |
| WO | 82/02819 | 9/1982 |
| WO | 1986/06082 | 10/1986 |
| WO | 89/01031 | 2/1989 |
| WO | 89/10960 | 11/1989 |
| WO | 1990/05765 | 5/1990 |
| WO | 1993/24142 | 12/1993 |
| WO | 97/38585 | 10/1997 |
| WO | 1997/38585 | 10/1997 |
| WO | 1997/39759 | 10/1997 |
| WO | 98/34498 | 8/1998 |
| WO | 1998/34498 | 8/1998 |
| WO | 99/39589 | 8/1999 |
| WO | 1999/39589 | 8/1999 |
| WO | 2000/23546 | 4/2000 |
| WO | 2000/25608 | 5/2000 |
| WO | 2000/38708 | 7/2000 |
| WO | 2001/028526 | 4/2001 |
| WO | 2001/082928 | 11/2001 |
| WO | 2002/083122 | 10/2002 |
| WO | 2002-083122 | 10/2002 |
| WO | 2002/092540 | 11/2002 |
| WO | 02/102394 | 12/2002 |
| WO | 2002/102394 | 12/2002 |
| WO | 2003/011873 | 2/2003 |
| WO | 2003/013497 | 2/2003 |
| WO | 2004/028529 | 4/2004 |
| WO | 2004/047554 | 6/2004 |
| WO | 2004/112767 | 12/2004 |
| WO | 05/004593 | 1/2005 |
| WO | 2005-018632 | 3/2005 |
| WO | 2005/037848 | 4/2005 |
| WO | 2005/038037 | 4/2005 |
| WO | 2005/070411 | 8/2005 |
| WO | 2006/030552 | 3/2006 |
| WO | 2004-100943 | 5/2006 |
| WO | 06/111633 | 10/2006 |
| WO | 07/080515 | 7/2007 |
| WO | 2007/080514 | 7/2007 |
| WO | 2007/080515 | 7/2007 |
| WO | 2007/108702 | 9/2007 |
| WO | 07/123424 | 11/2007 |
| WO | 2008/006607 | 1/2008 |
| WO | 08/072563 | 6/2008 |
| WO | 08/117062 | 10/2008 |
| WO | 2008/117062 | 10/2008 |
| WO | 2009/027692 | 3/2009 |
| WO | 2010/097701 | 9/2010 |
| WO | 2011/050474 | 5/2011 |
| WO | 2013/102792 | 7/2013 |
| WO | 2014/013335 | 1/2014 |

OTHER PUBLICATIONS

Valeri, D., et al., "Visocities of Fatty acids, triglycerides and their binary mixtures," JAOCS 74 (1997) pp. 1221-1226.

CRC 2013-2014, 94th ed., pp. 6-231-6-235.

EP Opposition filed Feb. 13, 2014 by Olympic Seafood AS, EP Patent Application No. EP08718910I6.

Brzustowicz, Michael R., et al., "Controlling Membrane Cholesterol Content. A Role for Polyunsaturated (Docosahexaenoate) Phospholipids," Biochemistry (2002), 41, pp. 12509-12519.

Jong-Ho Lee, "A Review: Antioxygenic and Peroxide-decomposing Activities of Antarctic Krill Lipids," J. Korean Soc. Food Mutr. 13(3) pp. 326-333 (1984).

Ki Woong Cho, et al., "Lipid and Fatty Acid Composition of the Antarctic Krill *Euphausia superba*," Ocean Research 21(2): 109-116 (1999).

Hvattum, Erlend, et al., "Effect of soybean oil and fish oil on individual molecular species of Atlantic salmon . . . ", Journal of Chromatography B, 748 (2000) 137-149.

(56) References Cited

OTHER PUBLICATIONS

Igarashi, Daisuke, et al., "Positional Distribution of DHA and EPA in Phosphatidylcholine and Phosphatidylethanolamine from Different Tissues of Squids," J. Oleo Sci. vol. 50, No. 9 (2001).
Tochizawa, Kaoru, et al., "Effects of Phospholipds Containing Docosahexaenoic Acid on Differentiation and Growth of HL-60 Human Promyelocytic Leukemia Cells," J. Jpn. Oil Chem. Soc. vol. 46, No. 4 (1997).
Zerouga, Mustapha, et al., "Comparison of phosphatidylcholines containing one or two docosahexaenoic acyl chains on properties of phospholipid monolayers and bilayers," Biochimica et Biophysica Acta 1236 (1995) 266-272.
Eung-Ho Lee, et al., "Studies on the Processing of Krill Sauce," J. Korean Soc. Food Nutr. 13(1) 97-106 (1984).
Hyun-Ku Kim, et al., "Effects of Cooking and Drying Methods on the Polar Lipds Composition of Shrimp," Korean J. Food Sci. Technol. vol. 21, No. 1, pp. 25-30 (1989).
Shon, Mi-Yae, et al., "Effects of Krill and Cadmium on Lipid Composition of Plasma in Cholesterol-Fed Rats," J. Korean Soc. Food Nutr. 23(1), 38-43 (1994).
Summons Materials downloaded from ESPACE on Dec. 16, 2014 for EP Patent Application No. 08 718 910.6.
Yanase, M., "Innovations on the russian method for separating heat coagulated protein from antarctic krill, through autolysis," Bulletin of Tokai Regional Fisheries Research Laboratory, 1974, No. 78, p. 79-84.
Kolakowski and Gajowiecki, "Optimization of autoproteolysis to obtain and edible product 'precipitate' from Antarctic krill," Seafood Science and Technology, pp. 331-336.
EP Opposition filed May 8, 2015 by Olympic Seafood AS, EP Patent No. 2144618, 150 pages.
Allahpichay et al., "Extraction of Growth Promoting Fractions from Non-muscle Krill Meal of Euphausia superba and its Effect on Fish Growth," Bulletin of the Japanese Society of Scientific Fisheries, 1984, 50(5): 821-826.
International Search Report, International Patent Application No. PCT/IB2016/000208, dated May 13, 2016, five pages.
Partial International Search Report, International Patent Application No. PCT/IB2016/000326, dated Jun. 15, 2016, six pages.
Database FSTA [Online} International Food Information Service, Frankfurt-Main; Shibata N. "Effect of fishing season on lipid content and composition of Antarctic krill (translated)" Database accession No. FS-1985-04-r-0091, abstract only.
Statement of Grounds and Particulars, Rimfrost AS, filed Jun. 10, 2016, Australian Patent Application No. 2014203179, 21 pages.
Takaichi et al., 2003, "Fatty Acids of astaxanthin esters in krill determined by mild mass spectrometry", Comparative Biochemistry and Physiology Part B, Biochemistry and Molecular Biology, Elsevier, Oxford, vol. 136, Jan. 1, 2003, p. 317-322.
Tanaka et al., 2004, "Extraction of Phospholipids from Salmon Roe with Supercritical Carbon Dioxide and an Entrainer", J. Oleo Sci, 53(9): 417-424.
Tanaka et al., 2005, "Extraction of Phospholipids from Unused Natrual Resources with Supercritical Carbon Dioxide and an Entrainer", Journal of Oleo Science, vol. 54(11): 569-576.
Todoric et al., 2006, "Adipose tissue inflammation induced by high-fat diet in obese diabetic mice is prevented by n-3 polyunsaturated fatty acids", Diabetologia, 49(9): 2109-2119.
Tou et al., 2007, "Krill for human consumption: nutritional value and potential health benefits.", Nutrition Rev 65(2):63-77.
Trayhurn et al., 2004, "Adipokines: inflammation and the pleiotropic role of white adipose tissue", Br. J. Nutrition, 92(3): 347-355.
Trebble et al., 2003, "Inhibition of tumour necrosis factor-alpha and interleukin 6 production by mononuclear cells following dietary fish-oil supplementation in healthy men and response to antioxidant co-supplementation", Br. J. Nutrition, 90(2): 405-412.
Ukkola et al., 2002, "Adiponectin: a link between excess adiposity and associated comorbidities?", J. Mol. Med., 80(11): 696-702.

Van Der Veen et al., 1971 "The Lipids of Krill (*Euphausia* Species) and Red Crab (*Pleuroncodes planipes*)", Lipids, 6(7): 481-485.
Virtue, et al. 1996, Reproductive trade-off in male Antarctic krill, *Euphausia superba*, Marine Biology, vol. 126, No. 3, pp. 521-527.
Yamaguchi et al., 1983, "The Composition of Carotenoid Pigments in the Antarctic Krill *Euphausia superba*", Bulletin of the Japanese Society of Scientific Fisheries, 49(9): 1411-1415.
Yamaguchi et al., 1986, "Supercritical Carbon Dioxide Extraction of Oils From Antarctic Krill," Journal of Agricultural and Food Chemistry, vol. 34, pp. 904-907.
Yanase M; 1974, "Modification of a Russian method for separation of heat-coagulated protein from Antarctic krill", Database FSTA (online); International Food Information Service (IFIS); Frankfurt-Main, DE.
Yen et al., 1994, "Effect of dietary omega-3 and omega-6 fatty acid sources on PUVA-induced cutaneous toxicity and tumorogenesis in the hairless mouse", Arch. Dermatol. Res., 286(6): 331-6.
Database WPI Week 200682, Thomson Scientific, London, GB, 2006.
Yanase, M., "Modification of Russian Method for Separating Heat Congulated Protein from Antarctic Krill," Bull. Tokai Reg. Fish. Res. Lab, 78: 79-84 (1974).
Sikorski, E., "The Utilization of Krill for Food," Food Process Eng., 1:845-855 (1980).
Budzinskli, E., et al., "Possibilities of processing and marketing of products made from Antarctic Krill", FAO Fish. Tech. Pap. (268) 46 pages (1985) (Budzinski).
Bunea R., et al.., "Evaluation of the Effects of Neptune Krill Oil on the Clinical Course of Hyperlipidemia," Alternative Medicine Review, Thorne Research Inc., Sandpoint, US, vol. 9, No. 4, Jan. 1, 2004.
Gordeev, K.Y., et al. "Fatty Acid Composition of the Main Phospholipids of the Antarctic Krill, *Euphausia superba*," Khim. Prirod. Soed. 2 (1990), pp. 181-187.
Dec. 8, 2011 Office Action, KR Patent Application No. 10-2010-7006897 and its English translation.
JP Office Action dated Feb. 23, 2012, JP Patent Application No. 2010-522444 (and English translation).
CN Office Action dated Apr. 27, 2012, JP Patent Application No. 200880112125.6 (and English translation).
Fricke, et al., Lipid, Sterol and Fatty Acid Composition of Antarctic Krill (*Euphausia superba* Dana), Lipids (1984) 19(11): 821-827.
Fricke, et al., 1-O-Alkylglycerolipids in Antarctic Krill (*Euphausia superba* Dana), Comp. Biochem. Physiol. (1986) 85B(1): 131-134.
Gordeev, K.Y., et al. "Fatty Acid Composition of the Main Phospholipids of the Antarctic Krill, *Euphausia superba*," Chem. Nat. Cmpds. (1990) 26(2), pp. 143-147.
Grantham (1977) Southern Ocean Fisheries Survey Programme, FAO Rome, GLO/SO/77/3: 1-61.
Raventos et al., Application and Posssibilities of Supercritical CO2 Extraction in Food Processing Industry: An Overview, Food Science and Technology International (2002) 8: 269-284.
Tanaka, T., et al., Platelet-activating Factor (PAF)-like Phospholoipds Formed during Peroxidation of Phosphatidylcholines from Different Foodstuffs, Biosci. Biotech. Biochem. (1995) 59 (8), pp. 1389-1393.
Winther, et al., Elucidation of Phosphatidylcholine Composition in Krill Oil Extracted from Euphausia superba, Lipids (2011)46: 25-36.
"Neptune Technologies & Bioressources Soon to Obtain a Major Patent in Over 30 Countries" ("2001 Press Release,").
Action Closing Prosecution, '348 patent.
Apr. 2, 2012 Response to Office Action, '351 patent.
Balassa et al., Microencapsulation in the Food Industry, Critical Reviews in Food Technology, 2:2, 245-265 (1971) ("Balassa").
Bell and Dick, Molecular Species Composition of the Major Diacyl Glycerophospholipids from Muscle, Liver, Retina and Brain of Cod (*Gadus morhua*), Lipids, vol. 26, No. 8, pp. 565-573 (1991) ("Bell and Dick").
Bell, Molecular Species Analysis of Phosphoglycerides from the Ripe Roes of Cod, Lipids, vol. 24, No. 7 (1989).

(56) References Cited

OTHER PUBLICATIONS

Bell, Molecular Species Composition of Phosphatidylcholine from Crypthecodinium cohnii in Relation to Growth Temperature Lipids 25, 115-118 (1990).

Bergelson (ed.), Lipid Biochemical Preparations, Chapter I.1, pp. 1-13 (1980).

Bottino N.R., "Lipid Composition of Two Species of Antarctic Krill: *Euphausia superba* and *E. crystallorophias*," Comp. Biochem. Physiol., 1975, vol. 50B, pp. 479-484.

Buchi R-220 Rotovapor® Manual.

Buda, Structural order of membranes and composition of phospholipids in fish brain cells during thermal acclimatization, Proc. Natl. Acad. Sci. USA vol. 91, pp. 8234-8238, Aug. 1994.

Certificate of translation of Ex. 1072: Fisheries Agency, General Report on Research and Development of Techniques in Processing and Utilization of Marine Products, Chapter 6, Development of technology for recovery of valuable substances (astaxanthin) from krill, by Takao Fujita, pp. 273-307 (Mar. 1985); Japanese language document.

Certificate of translation of Ex. 1074: Japanese Patent No. 60-153779, entitled "Nutritional Supplement".

Certificate of translation of Ex. 1076: Japanese Patent Publication No. H08-231391, entitled "Medicine for Improvement of Dementia Symptoms".

Certification of translation of Ex. 1070: Japanese Unexamined Patent Application Publication No. 02-215351.

Certified translation of Ex. 1070: Japanese Unexamined Patent Application Publication No. 02-215351, titled Krill Phospholipids Fractioning Method ("Maruyama,"); Certificate of Translation provided as Ex. 1071.

Certified translation of Ex. 1072: Fisheries Agency, General Report on Research and Development of Techniques in Processing and Utilization of Marine Products, Chapter 6, Development of technology for recovery of valuable substances (astaxanthin) from krill, by Takao Fujita, pp. 273-307 (Mar. 1985) ("Fujita") ; Certificate of Translation Provided as Ex. 1073.

Certified translation of Ex. 1074: Japanese Patent No. 60-153779, entitled "Nutritional Supplement" ("Fukuoka"); Certificate of Translation provided as Ex. 1075.

Certified translation of Ex. 1076: Japanese Patent Publication No. H08-231391, entitled "Medicine for Improvement of Dementia Symptoms" ("Yasawa"); Certificate of Translation provided as Ex. 1077.

Declaration of Bjorn Ole Haugsgjerd in support of Inter Partes Review of U.S. Pat. No. 8,278,351.

Ando and Hatano, 1988, "Isolation of apolipoproteins from carotenoid-carrying lipoprotein in the serum of chum salmon, *Oncorhynchus keta*", J. Lipid Research, 29: 1264-1271.

Aoi et al., 2003, "Astaxanthin limits exercise-induced skeletal and cardiac muscle damage in mice", Antioxidants & Redox Signaling, 5(1): 139-44.

Britton, 1985, "General Carotenoid Methods", Methods in Enzymology, vol. 111, pp. 113-149.

Calder, 2006, "n-3 polyunsaturated fatty acids, inflammation, and inflammatory diseases", Am. J. Clin. Nutr., 83: 1505S.

Charest et al., 2001, "Astaxanthin Extraction from Crawfish Shells by Supercritical CO2 with Ethanol as Cosolvent", J. Aquatic Food Product Technology, 10(3): 79-93.

Chen and Meyers, 1982, "Extraction of Astaxanthin Pigment from Crawfish Waste Using a Soy Oil Process", J. Food Sci., 47: 892-896.

Clarke, 1980, "The Biochemical Composition of Krill, *Euphausia superba* dana,from South Georgia", J. Exp. Mar. Biol. Ecol., 43: 221-236.

Czeczuga, 1974, "Comparative Studies of Carotenoids in the Fauna of the Gullmar Fjord (Bohuslan, Sweden). II. Crustacea: *Eupagurus bernhardus*, *Hyas coarctatus* and *Upogebia deltaura*", Marine Biology, 28: 95-98.

De Ritter and Purcell, 1981, "Carotenoid Analytical Methods", Carotenoids as Colorants and Vitamin A Precursors: Technological and Nutritional Applications, pp. 815-882.

Deutch, 1995, "Menstrual pain in Danish women correlated with low n-3 polyunsaturated fatty acid intake", Eur. J. Clin. Nutr., 49(7): 508-16.

Diez et al., 2003, "The role of the novel adipocyte-derived hormone adiponectin in human disease", Eur. J. Endocrinol., 148(3): 293-300.

Ellingsen et al., 1987, "Biochemistry of the autolytic processes in Antarctic krill post modem. Autoproteolysis." Biochem. J. 246, 295-305.

Emodi, 1978, "Carotenoids: Properties and Applications", Food Technology, 32(5): 38.

Felix-Valenzuela et al., 2001, "Supercritical CO2/Ethanol Extraction of Astaxanthin from Blue Crab (*Callinectes apidus*) Shell Waste", Journal of Food Process Engineering, 24: 101-112.

Fox and Scheer, 1941, "Comparative Studies of the Pigments of Some Pacific Coast Echinoderms", The Biological Bulletin, 441-455.

Geusens et al., 1994, "Long-term effect of omega-3 fatty acid supplementation in active rheumatoid arthritis. A 12-month, double-blind, controlled study", Arthritis Rheum., 37(6): 824-9.

Gilchrist and Green, 1960, "The Pigments of Artemia", Proceedings of the Royal Society, Series B Biological Sciences, vol. 152 No. 946, pp. 118-136.

Goodwin and Srisukh, 1949, "Some Observations on Astaxanthin Distribution in Marine Crustacea", Department of Biochemistry, University of Liverpool, pp. 268-270.

Gulyaev and Bugrova, 1976 "Removing fats from the protein paste Okean". Konservnaya I Ovoshchesushil'naya Promyshlennost, (4), 37-8.

Hardardottir and Kinsella, 1988, "Extraction of Lipid and Cholesterol from Fish Muscle with Supercritical Fluids" Journal of Food Science, 53(6): 1656-1658.

International Aqua Feed, 2006, vol. 9.

International Search Report and Written Opinion for PCT/GB2008/002934, dated Mar. 11, 2009.

International Search Report and Written Opinion for PCT/IB2010/000512; dated Jun. 24, 2010.

International Search Report for PCT/IB2007/000098, dated Jun. 26, 2007.

Itoh et al., 2007; "Increased adiponectin secretion by highly purified eicosapentaenoic acid in rodent models of obesity and human obese subjects", Arteriosclerosis, Thrombosis, and Vascular Biology; 27(9): 1918-1925.

Johnson et al., 1978, "Simple Method for the Isolation of Astaxanthin from the Basidiomycetous Yeast *Phaffia rhodozyma*", Applied and Environmental Microbiology, 35(6): 1155-1159.

Kolakowska, 1989, "Krill lipids after frozen storage of about one year in relation to storage time before freezing", Die Nahrung Food, 33(3): 241-244.

Kris-Etherton et al., 2002, "Fish Consumption, Fish Oil, Omega-3 Fatty Acids, and Cardiovascular Disease", Circulation, 106:2747-2757.

Kristensen et al., 1989, "Dietary supplementation with n-3 polyunsaturated fatty acids and human platelet function: a review with particular emphasis on implications for cardiovascular disease", J. Intern. Med. Suppl. 731:141-50.

Kunesova et al., 2006, "The influence of n-3 polyunsaturated fatty acids and very low calorie diet during a short-term weight reducing regimen on weight loss and serum fatty acid composition in severely obese women", Physiol Res.; 55 (1):63-72.

Laight et al., 1999, "F2-isoprostane evidence of oxidant stress in the insulin resistant, obese Zucker rat: effects of vitamin E", Eur. J. Pharmacol. 377(1): 89-92.

Lambertson and Braekkan, 1971, "Method of Analysis of Astaxanthin and its Occurrence in some Marine Products," J. Sci. Food. Agr., vol. 22(2): 99-101.

Libby et al., 2006, "Inflammation and Atherothrombosis: From Population Biology and Bench Research to Clinical Practice", J. Amer. Coll. Card., 48 (9, Suppl. A): A33-A46.

Lopez et al., 2004, "Selective extraction of astaxanthin from crustaceans by use of supercritical carbon dioxide", Talanta, 64: 726-731.

(56) References Cited

OTHER PUBLICATIONS

Mandeville, 1991, "Isolation and Identification of Carotenoid Pigments, Lipids and Flavor Active Components from Raw Commercial Shrimp Waste", Food Biotechnology, 5(2): 185-195.
Meyers and Bligh, 1981, "Characterization of Astaxanthin Pigments from Heat-Processed Crawfish Waste", J. Agric. Food Chem., 29: 505-508.
Myers, 1977, "Using Crustacean Meals and Carotenoid-Fortified Diets", Feedstuffs, vol. 49(19).
Meyers, 1994, "Developments in world aquaculture, feed formulations, and role of carotenoids", Pure & Appl. Chem, vol. 66(5): 1069-1076.
Mills et al., 1989, "Dietary N-6 and N-3 fatty acids and salt-induced hypertension in the borderline hypertensive rat", Lipids, 24(1): 17-24.
Moates and Van Bentem, 1990, "Separating out the value", Food Science and Technology Today, 4(4): 213-214.
Nikolaeva, 1967 "Amino acid composition of protein-coagulate in krill", VNIRO, 63:161-4.
Phleger, et al. (2002) "Interannual and between species comparison in the lipids, fatty acids, and sterols of Antarctic krill from the US AMLR Elephant Island survey area: 1997 and 1998". Comp Biochem Physiol 131B:733-747.
Popp-Snijders et al., 1987, "Dietary supplementation of omega-3 polyunsaturated fatty acids improves insulin sensitivity in non-insulin-dependent diabetes", Diabetes Res. 4(3): 141-7.
Sachindra, 2006, "Recovery of carotenoids from shrimp waste in organic solvents", Waste Management, 26: 1092-1098.
Saether et al., 1986, "Lipids of North Atlantic krill", J Lipid Res., 27(3):274-85.
Shahidi et al., 1998, "Carotenoid Pigments in Seafoods and Aquaculture" Critical Reviews in Food Science, 38(1): 1-67.
Sidehu et al., 1970, "Biochmical Composition and Nutritive Value of Krill (*Euphausia superb* dana)", J. Sci Food Agr., vol. 21, 293-296.
Simopoulos, 1991, "Omega-3 fatty acids in health and disease and in growth and development", Am. Clin. Nutr. 54:438-63.
Somiya, 1982, "'Yellow lens' eyes of a stomiatoid deep-sea fish, *Malacosteus niger*", Proc. R. Soc. Lond., 215: 481-489.
Declaration of Bjorn Ole Haugsgjerd submitted during inter partes reexamination of parent U.S. Pat. No. 8,030,348 ("Haugsgjerd '348 Decl.").
Declaration of Dr. Albert Lee in Support of Inter Partes Review of U.S. Pat. No. 8,278,351 ("Lee").
Declaration of Dr. Albert Lee in Support of Inter Partes Review of U.S. Pat. No. 8,383,675 ("Lee").
Declaration of Dr. Chong Lee submitted during inter partes reexamination of parent U.S. Pat. No. 8,030,348 ("Yeboah Reexam Decl.").
Declaration of Dr. Earl White submitted during prosecution of parent U.S. Pat. No. 8,030,348 ("2011 White Decl.").
Declaration of Dr. Ivar Storrø in support of Inter Partes Review of U.S. Pat. No. 8,278,351 ("Storrø").
Declaration of Dr. Ivar Storrø in support of Inter Partes Review of U.S. Pat. No. 8,383,675 ("Storrø").
Declaration of Dr. Jacek Jaczynski from inter partes reexamination of the parent U.S. Pat. No. 8,030,348 ("Jaczynski Reexam. Decl.").
Declaration of Dr. Jaczynski submitted during prosecution of parent U.S. Pat. No. 8,278,351 (Jaczynski '351 Decl.).
Declaration of Dr. Jeff Moore in Support of Inter Partes Review of U.S. Pat. No. 8,278,351 ("Moore").
Declaration of Dr. Jeff Moore in Support of Inter Partes Review of U.S. Pat. No. 8,383,675 ("Moore").
Declaration of Dr. Richard van Breemen in Support of Inter Partes Review of U.S. Pat. No. 8,278,351 ("Van Breemen").
Declaration of Dr. Richard van Breemen in Support of Inter Partes Review of U.S. Pat. No. 8,383,675 ("Van Breemen").
Declaration of Dr. Shahidi submitted during inter partes reexamination of parent U.S. Pat. No. 8,030,348 (Shahidi Reexam. Decl.).
Declaration of Dr. Shahidi submitted during prosecution of parent U.S. Pat. No. 8,278,351 (Shahidi '351 Decl.).
Declaration of Dr. Suzanne Budge in Support of Inter Partes Review of U.S. Pat. No. 8,278,351 ("Budge").
Declaration of Dr. Suzanne Budge in Support of Inter Partes Review of U.S. Pat. No. 8,383,675 ("Budge").
Declaration of Dr. Thomas Brenna in support of Inter Partes Review of U.S. Pat. No. 8,278,351.
Declaration of Dr. Thomas Brenna in support of Inter Partes Review of U.S. Pat. No. 8,383,675.
Declaration of Dr. Thomas Gundersen submitted during inter partes reexamination of parent U.S. Pat. No. 8,030,348 ("Gundersen Decl.").
Declaration of Dr. Tina Sampalis submitted during inter partes reexamination of parent U.S. Pat. No. 8,030,348 (Sampalis).
Declaration of Dr. Van Breemen submitted during Ex parte Reexamination of the '351 patent (Van Breemen '351 Reexam. Decl.
Declaration of Dr. Van Breemen submitted during Inter partes Reexamination of the '348 patent (Van Breemen '348 Reexam Decl.
Declaration of Dr. Yeboah submitted during inter partes reexamination of parent U.S. Pat. No. 8,030,348 ("Yeboah Reexam Decl.").
Declaration of Dr. Yeboah submitted during prosecution of parent U.S. Pat. No. 8,278,351 ("Yeboah '351 Decl.").
Eichberg, "Lecithin—It Manufacture and Use in the Fat and Oil Industry," Oils and Soap 51-54, 1939 ("Eichberg").
Expert Witness Report of Dr. Theodore Welch submitted in relation to ITC Investigation No. 337-TA-877 ("Welch").
Farkas, Composition and Physical State of Phospholipids in Calanoid Copepods from India and Norway, LIPIDS, vol. 23, No. 6 (1988).
Final Prospectus dated May 11, 2001 ("Final Prospectus").
Folch, et al., A Simple Method for the Isolation and Purification of Total Lipids from Animal Tissues. J. Biol. Chem., 226, 497-509 (1957).
Grant of Request for Ex parte Reexamination of the '351 patent.
Grit et al., Hydrolysis of phosphatidylcholine in aqueous liposome dispersions, Int. J. Pharmaceutics 50:1-6 (1989).
Henderson et al., Lipid Composition of the Pineal Organ from Rainbow Trout (*Oncorhynchus mykiss*), Lipids, vol. 29, No. 5, pp. 311-317 (1994) ("Henderson").
Herman and Groves, The Influence of Free Fatty Acid Formation on the pH of Phospholipid-Stabilized Triglyceride Emulsions, Pharmaceutical Research 10(5):774-776 (1993).
Itano Refrigerated Food Co., Ltd., Bio & High Technology Announcement and Natural Astaxanthin & Krill Lecithin, pp. 1-16 (on or before Dec. 28, 1994) ("Itano").
Johnson and Lucas, Comparison of Alternative Solvents for Oils Extraction, JAOCS 60(2):229-242 (1983).
Le Grandois et al., Investigation of Natural Phosphatidylcholine Sources: Separation and Identification by Liquid Chromatography-Electrospray Ionization-Tandem Mass Spectrometry (LC-ESI-MS2) of Molecular Species, J. Agric. Food Chem., 57, 6014-20 (2009) ("Le Grandois").
Lin et al., Effect of Dietary N-3 Fatty Acids Upon the PhospholipidMolecular Species of the Monkey Retina, Invest Ophthalmol Vis Sci. 1994;35:794-803.
Medina et al., C Nuclear Magnetic Resonance Monitoring of Free Fatty Acid Release After Fish Thermal Processing, J. Amer. Oil Chem. Soc. 71(5):479-82 (1994).
Oct. 24, 2012 Office Action, '675 patent.
Office Action dated Jan. 5, 2012, '351 patent.
U.S. Appl. No. 60/307,842 (Priority document for the '351 patent).
Supplemental Declaration of Bjorn Ole Haugsgjerd submitted during inter partes reexamination of parent U.S. Pat. No. 8,030,348 ("Haugsgjerd '348 Supp. Decl.").
Supplemental Declaration of Dr. Earl White submitted during inter partes reexamination of parent U.S. Pat. No. 8,030,348 ("White Supp. Reexam. Decl.").
Supplemental Declaration of Dr. Earl White submitted during prosecution of parent U.S. Pat. No. 8,278,351 ("White Supp. Decl.").

(56) References Cited

OTHER PUBLICATIONS

Supplemental Declaration of Dr. Thomas Gundersen submitted during inter partes reexamination of parent U.S. Pat. No. 8,030,348 ("Gundersen Supp. Decl.").
Suzuki, T. and Shibata, N., "The utilization of Antarctic krill for human food," Food Rev. Int'l, 6:1, 119-147 (1990) ("Suzuki").
Takahashi et al., Compositional Changes in Molecular Species of Fish Muscle Phosphatidylcholine During Storage, Bull. Fac. Fish. Hokkaido Univ. 37(1), 80-84 1986.
Takahashi et al., Molecular Species of Fish Muscle Lecithin, Bulletin of the Japanese Society of Scientific Fisheries 48(12), 1803-1814 (1982).

\* cited by examiner

PHOSPHOLIPID COMPOSITIONS AND THEIR PREPARATION

This application is a U.S. 371 national phase entry of International Patent Application No. PCT/EP2015/050370, international filing date Jan. 9, 2015, which claims the benefit of United Kingdom patent application 1400431.1 filed Jan. 10, 2014, the complete contents of which are incorporated herein by reference for all purposes.

TECHNICAL FIELD

The present invention provides phospholipid compositions which are suitable for pharmaceutical purposes, and to improved processes for preparing them.

BACKGROUND OF THE INVENTION

There is accumulating evidence of the benefits of dietary intake of the long chain omega-3 fatty acids found in fish, docosahexaenoic acid (DHA) and eicosapentaenoic acid (EPA). These fatty acids have been shown to decrease the risk of coronary heart disease and ischemic heart disease in large epidemiological studies.

Omega-3 fatty acids have furthermore been proposed for a variety of medical uses, including prevention of heart disease, diabetes, inflammation, depression, Alzheimer's and attention deficit disorder. Examples of pharmaceuticals based on omega-3 fatty acids include Lovaza® (known also as Omacor®) which is approved in various countries for treatment of patients with very high triglycerides (hypertriglyceridemia), and for post myocardial infarction adjuvant treatment in secondary prevention after myocardial infarction. In Lovaza® the omega-3 fatty acids are present as ethyl esters. Each Lovaza® 1 gram capsule contains 465 mg EPA ethyl ester, 375 mg DHA ethyl ester, 80 mg of other omega-3 fatty acids, 30 mg of omega-6 fatty acids and 50 mg of antioxidants.

Vascepa® (AMR-101) is a further approved pharmaceutical based on omega-3 fatty acids. Vascepa® capsules contain EPA omega-3 fatty acid in the form of ethyl eicosapentaenoic acid. Vascepa® has been clinically proven to significantly reduce triglyceride levels without increasing LDL-C. It has been approved in the United States for use as an adjunct to diet to reduce triglyceride levels in adult patients with severe (≥500 mg/dL) hypertriglyceridemia.

There is growing evidence, however, that the molecular form of omega-3 fatty acids (e.g. triglycerides or ethyl esters) might be of importance for their biological effect and for their distribution in the body. Krill oil contains a high proportion of omega-3 fatty acids incorporated in phospholipids and it has been demonstrated that krill oil had stronger effects than fish oil on specific parameters related to metabolic syndromes [1]. The authors suggest that this difference may be linked to differences in the incorporation of omega-3 fatty acids into membranes. Further, it was demonstrated that the level of DHA in the brain increased significantly after krill oil administration when compared to control animals [2]. Thus, omega-3 fatty acids incorporated in phospholipids may be differently distributed in the body compared to omega-3 fatty acids in other molecular forms.

The concentration of phospholipids in commercially available krill oils is relatively low. For example, they can include high amounts of neutral lipids and free fatty acids. Although krill extracts with 90% phospholipid have been described [3], these contain undesirable components such as lysophospholipids and astaxanthins, and their preparation has involved the use of solvent systems which are not favourable for downstream pharmaceutical use. Thus there is a need for krill phospholipid compositions having a high purity without retaining pharmaceutically undesirable solvents or components, and also for processes by which such compositions can be prepared.

DISCLOSURE OF THE INVENTION

The invention provides improved processes for extracting and preparing polar lipids (in particular, desirable phospholipids) from krill and other biological sources. The inventors have discovered processes through which it is possible to extract phospholipids to give high phospholipid content and a reduction of undesired components.

Processes of the Invention

The invention provides a process for preparing a composition which is rich in polar lipids from a biological material containing those lipids, comprising steps of:
  (a) mixing the biological material with a first solvent system in which the polar lipids are soluble, thereby preferentially extracting the polar lipids into a liquid phase of a slurry;
  (b) washing the biological material with a second solvent system in which the polar lipids are poorly soluble; and
  (c) mixing the extracted and washed material from steps (a) and (b) with a third solvent system which partitions neutral lipids and polar lipids,
wherein steps (a) and (b) can be performed in either order before step (c).

The process takes advantage of the different solubility of the various components of the biological material in three different solvent systems. For example, the polar nature of the desired lipids means they can behave differently from neutral lipids in certain solvents. These differences allow the different lipids to be separated effectively during the process of the invention, resulting in material having a high content of the desired lipids, and in which the content of undesirable components is reduced. In particular the relatively high solubility of the desired polar lipids in certain solvents (the first solvent system e.g. concentrated organic protic solvents) allows their efficient extraction from biological materials, whereas their relatively low solubility in other solvents (the second solvent system e.g. a dilute organic protic solvent) means that such solvents can be used to wash out various undesired components from the lipid material. Finally, although the polar lipids and various neutral lipids may both be soluble in the first solvent system, they have different properties which means that they can be separated in a further treatment step, which also serves to reduce the concentration of other undesired components. Overall, the process of the invention can efficiently reduce the amount of (or even remove) various undesired components including trimethylamine N-oxide (TMAO), astaxanthins, lysophospholipids, free fatty acids, cholesterol and cholesterol esters, and neutral lipids. Furthermore, the process can be used with three solvent systems which are all readily acceptable for pharmaceutical purposes and whose solvent components (particularly their organic components) can if necessary be removed to safe residual levels.

The process has been designed to increase the proportion of phospholipids in the final composition relative to undesired components. At any stage of the process, the ratio of phospholipids to any specific undesired component can be determined and the ratio calculated. The ratio is in general calculated on a weight/weight basis. Where possible, undesired components can be removed completely i.e. to be un-quantifiable in the final composition (using currently available analytical techniques i.e. below the limit of quantification or LOQ).

Step (a)

Step (a) of the process involves mixing a biological material with a first solvent system in which the polar lipids are soluble, to preferentially extract polar lipids into a liquid phase of a slurry. The desired polar lipids in the biological material are thus solubilised for further processing and extraction. The solubility of the biological material's various components in the first solvent system will determine their location at the end of step (a). Components that are soluble in the first solvent system (including the desired polar lipids) will tend to be extracted from the biological material, so that they are present in the liquid phase at the end of step (a). Other components will preferentially remain in the slurry residue. Key components which are present primarily in the slurry after step (a) are triglycerides, proteins/peptides, and insoluble materials such as shell fragments (calcium carbonate, chitosan, etc.), but also cholesterol esters.

The desired lipids are soluble in the first solvent system and so they are preferentially extracted into the slurry's liquid phase, from which they can be processed further. The term "preferentially" is used to reflect the fact that the desired polar lipids tend to be more soluble than neutral lipids in the liquid phase. The polar lipids will thus tend to enter the liquid phase, rather than remaining with the biological material slurry. Other lipids present in the biological material (e.g. neutral lipids) tend to be less soluble in the liquid phase and so some of these remain with the slurry. The term "preferentially" thus also reflects the fact that although some neutral lipids might be present in the liquid phase at the end of step (a), the liquid phase will contain a higher ratio of polar lipids:neutral lipids compared to the ratio in the biological material at the start of step (a). In contrast, the slurry residue will contain a lower ratio of polar lipids: neutral lipids compared to the starting biological material. For example, krill material may contain a weight ratio of phospholipids:neutral lipids which is approximately 1:1 before step (a), whereas this can be 4:1 or higher in the liquid phase after step (a). The ratio of phospholipids to neutral lipids in the liquid phase after step (a) is thus higher than in the material before step (a). Moreover, the ratio of phospholipids to triglycerides can be about 10:1 in the liquid phase after step (a).

The solvent system used in step (a) (the 'first' solvent system) is any solvent system whose addition to the biological material results in a liquid phase in which polar lipids are preferentially soluble relative to neutral lipids. The solvent system can be a mixture of solvent components. The first solvent system will generally comprise at least one protic solvent component and an organic solvent component (or, more usually, an organic protic solvent).

Typical organic protic solvents or solvent components for use in step (a) include, but are not limited to, n-butanol, n-propanol, isopropanol, nitromethane, ethanol, and methanol. Hydroxy-containing protic solvents are preferable, and the most preferred organic solvent for use with the invention is ethanol. The amount and concentration of organic protic solvent components which are used is enough to provide a first solvent system which can preferentially extract the desired lipids into a liquid phase of a slurry. The amount and concentration of organic solvent components will take into account the amount of moisture that is present in the biological material at the start of step (a).

In one embodiment, the first solvent system comprises ethanol and water, ideally with a final ethanol concentration of between 70-95% w/w, or 80-90% w/w (based on total weight of solvent). If the starting material already includes water (which will usually be the case), the amount of ethanol that is added will take this water into account, and will also take into account the amount of any water in the ethanol (see below). By way of example, the weight ratio of ethanol: biological material is generally within the range of 1:1 to 10:1, preferably within the range of 2:1 to 8:1, or between about 3:1 to about 4:1. For instance, between 3-4 kg of absolute ethanol can be added per kg of wet krill material having a water content of 65% in order to provide the first solvent system, taking into account the water content of the krill material.

Step (a) may conveniently be performed at temperatures of up to 50° C. The biological material and solvent components which are added may be at different temperatures when they are first combined. For instance, the biological material might be frozen i.e. at a temperature of less than 0° C. e.g. less than about −5° C., −10° C., −15° C., −20° C., or −25° C. Solvent components should be liquid when they are added to the biological material, and are preferably at a temperature of between 0-50° C. e.g. at between 10-45° C., between 15-35° C. or 20-25° C. After mixing, however, the mixture can be incubated under room temperature conditions or within any temperature range referred to above e.g. at between 10-45° C. The temperature chosen for step (a) can represent a balance between higher yields and lower purity, and incubation at between 20-25° C. gives good results using krill material and ethanol.

Mixing of the biological material and the first solvent system ensures that they become distributed within each other. In some circumstances this might be achieved simply by combining two components, but usually it requires active mixing e.g. by stirring, inversion, or other appropriate means. Mixing is preferably achieved using stirring, which is preferably carried out at 50 to 500 rpm, or 100 to 200 rpm. Stirring or other active mixing steps may be continued for as long as desired to ensure adequate contact between different components, and this can usually be achieved in an hour or less, although longer periods can also be used (e.g. up to several weeks). Stirring in step (a) for 45 minutes can achieve a good extraction of polar lipids, but longer periods can increase the amount of material which is extracted e.g. for between 2-6 hours, such as for 3-4 hours.

After the biological material and the organic solvent components have been mixed, a slurry forms in which the desired lipids are preferentially present in a liquid phase. The liquid phase also contains other components from the biological material that are soluble in the first solvent system e.g. other polar lipids, some neutral lipids, some proteins, water soluble amines, and ionic species. This liquid phase is separated from the slurry and is processed further in downstream steps. Separation of the liquid phase from the slurry can be achieved by any suitable means for separating solids and liquids e.g. centrifugation, filtration, decanting, draining, etc.

If desired the slurry residue can be recycled, such that it is re-used as biological material for one or more repeats of step (a). In this manner it is possible to extract polar lipids which remain within the slurry residue. Such further extracted material can then continue into subsequent steps e.g. after being combined with other material arising from previous extractions.

If step (a) comes before step (b), the starting biological material is extracted as defined above, and the extracted polar lipids are then washed as described below in step (b). On the other hand, if step (a) comes after step (b), the starting biological material will previously have been washed as described below for step (b), it will then be extracted as discussed above, and these washed and extracted polar lipids will then be taken into step (c) as described below.

Step (b)

Step (b) of the process involves washing the biological material with a second solvent system in which the polar lipids are poorly soluble. This biological material may be the product of step (a), or may be biological material which is to be washed before extraction step (a) takes place.

The key difference between step (a) and (b) is that the desired polar lipids are highly soluble in the first solvent system but are poorly soluble in the second solvent system, while undesired components (such as salts, metal ions, carbohydrates) will dissolve in the second solvent system. Thus step (b) permits the biological material to be washed (before or after step (a) solubilises them), and this washing is useful for e.g. de-salting the material.

The choice of second solvent system can depend on whether step (b) occurs before or after step (a). For instance, if step (b) occurs before step (a) then the second solvent system might be achieved using water, or a weak aqueous solution of organic solvent, to wash the biological material, thereby dissolving undesired components into the water. The aim of this early washing is to remove undesired components which are soluble in water, without solubilising a significant amount of the desired polar lipids. If step (b) occurs after step (a), however, it is easier if the second solvent system is derived from the first solvent system e.g. by using a strong ethanol solution as the first solvent system and a weak ethanol solution as the second solvent system.

The change between the first and second solvent systems can be achieved in various ways. For example, if step (a) precedes step (b) then the first solvent system can be removed (e.g. by evaporation) and then the second solvent system can be added, but in some embodiments it is possible to simply dilute the first solvent system until the second solvent system is formed e.g. by adding more water to a strong ethanol solution (the first solvent system) to form a weak ethanol solution (the second solvent system). If step (a) follows step (b) then the second solvent system can be removed (e.g. by evaporation) and then the first solvent system can be added, but in some embodiments it is possible to simply add extra solvent components until the first solvent system is formed e.g. by adding more concentrated ethanol to a weak ethanol solution or to water (possible second solvent systems) to form a strong ethanol solution (the first solvent system).

Where solvent removal is used between steps (a) and (b) then evaporation is a convenient technique when the solvent includes components which are more volatile than water. Evaporation can provide material which is solid at room temperature and is moderately rich in polar lipids, suitable for washing. For instance, up to about 85% by weight of this lipid-rich material can be phospholipids of interest. The second solvent system can then be added to this material.

In general, however, the preferred way of making the second solvent system when step (b) follows step (a) is by dilution of the first solvent system. Dilution of the first solvent system, to reduce the overall concentration of its solvent components, is achieved by adding a diluent. Examples of suitable diluents include aqueous diluents such as water, but solutions of a solvent component (e.g. an organic protic solvent) which may be the same as or different to the solvent component used in step (a) may also be used. Preferably the concentration of a solvent component (e.g. an organic protic solvent such as ethanol) in the mixture after dilution is between 50-70% w/w (solvent/total weight of the liquid material). Appropriate solvent mixtures and concentrations for washing the phospholipids to remove impurities, without too much loss of the desired lipids, can vary with temperature and with the chosen solvent system, but can readily be assessed.

Thus the second solvent system when step (b) follows step (a) may be an aqueous solution of ethanol, where the concentration of ethanol is between 50-70% w/w, preferably between 55-65%, between 58-62%, or about 60%. Under typical conditions, ethanol concentrations above about 70% tend to lead to the loss of too much polar lipids in the waste, whereas concentrations below about 60% can lead to the formation of emulsions from which the polar lipids are difficult to extract.

The second solvent system when step (b) precedes step (a) may be a weak aqueous solution of ethanol (e.g. up to 10% w/w EtOH), but ideally use water.

Mixing with the second solvent system generally involves stirring to ensure that the materials become distributed within each other. Stirring is preferably carried out at 50 to 500 rpm, or 100 to 200 rpm. Stirring may be continued for as long as desired to ensure adequate contact, and this can usually be achieved less than an hour, although longer periods can also be used (e.g. several weeks). After stirring the mixture is allowed to settle, and it separates into phases which include a lipid-rich phase that can be processed further. The other phase(s) are referred to herein as the waste, which includes material which has been washed away using the second solvent system.

Compared to the material prior to step (b), the lipid-rich phase has an increased proportion of desired polar lipid components relative to certain undesired components. The solubility of certain undesired components in the second solvent system is such that they will tend to enter the waste phase(s), whereas the polar lipid components will tend to remain in the desired lipid-rich phase. The waste thus contains certain undesired components that are more water-soluble than the desired polar lipids. Examples of such components include salts such as TMAO, water soluble proteins and peptides, water soluble amines, salts such as NaCl and $CaCl_2$, other ionic species, and also lysophospholipids. The lipid-rich phase (which can be approximately 60% lipids and 40% solvent when step (b) follows step (a)) contains the desired phospholipids but also contains some neutral lipids (e.g. at a ratio of approximately 4:1 phospholipids to neutral lipids when step (b) follows step (a)).

The lipid-rich phase and the waste are separated before proceeding. This can be achieved simply by letting the mixture settle or by centrifugation, to produce a lipid-rich phase and a waste phase which are then separated e.g. by decanting, draining the lipid-rich phase, or suction of the waste phase. In general if the mixture is allowed to settle then the lipid-rich phase is underneath the waste phase. The mixture is generally allowed to settle for a sufficient period of time to allow the effective separation of the two phases. This may be at least 4 hours (e.g. at least 6, 8, 10, 12, 14, 16, 18, 20, 22, 24, 30, 36, 48, 54, 60 hours). This may be carried out at any suitable temperature, e.g. less than 50° C., 40° C., 30° C., 20° C., 10° C., 5° C. If step (b) precedes step (a) the liquid water phase is the waste, containing dissolved impurities. This is removed from the slurry, which is processed further in downstream steps. Separation of the liquid phase from the slurry can be achieved by any suitable means for separating solids and liquids e.g. centrifugation, filtration, decanting, draining, etc.

The lipid-rich phase contains a high proportion of desired polar lipids. This phase can be re-washed using step (b) again. The solvent system used for re-washing can conveniently be the same as the solvent system which was used for previous washing. For instance, if step (b) first used a 60% w/w ethanol solution then re-washing can also be achieved by adding ethanol and/or water to the lipid-rich phase to achieve a final concentration of 60% w/w ethanol. This can again provide a lipid-rich phase and a waste phase.

Thus, if desired, washing step (b) can be performed more than once, such that a washed lipid-rich phase is re-washed at least once under the same or similar conditions. Thus step (b) may include more than one wash e.g. it can include between 2-10 (e.g. 3-9, 4-8, 5-7) washings with a second solvent system. Performing multiple washes can remove undesired components which would otherwise remain in the lipid-rich phase. Repeated washings can also have a minor impact on the ratio of polar lipids to neutral lipids, as a small amount of polar lipids may enter the waste phase, but in general step (b) does not have a large impact on this ratio (e.g. when step (b) follows step (a) a change from 82:18 to 78:22 has been seen, so only a small amount of phospholipid was lost). Where multiple washings are used, it is possible to reduce the washing time as further steps are added e.g. an 8 hour duration for the first wash, then 7 hours for the second, and 6 hours for subsequent washes, etc.

Washing step (b) may be carried out at any suitable temperature but is optionally carried out at temperatures within the range of 5-25° C.

As noted above, an example of an undesired component affected by step (b) is TMAO (trimethylamine N-oxide, $(CH_3)_3NO$). This is an osmolyte found in saltwater fish, sharks and rays, molluscs, and crustaceans, which is believed to have a role in counteracting the protein-destabilizing effects of pressure. TMAO is highly soluble in water and will thus tend to enter the waste rather than the lipid-rich phase during step (b). The ratio of phospholipid:TMAO on a w/w basis is thus lower in the starting material than in the washed liquid phase which is produced in step (b). Based on experience with krill material, 85% of TMAO can be removed with a single washing step, and repeated washing can remove TMAO to levels below the LOQ.

Step (b) can also efficiently remove salts, such as sodium chloride, which can be seen by measuring conductivity of the material e.g. step (b) can reduce the material's conductivity to the same level as de-ionised water. Wet krill material can have a NaCl concentration of 1.5% by weight or more, but step (b) can reduce conductivity from several hundred µS/cm down to about 10 µS/cm.

Step (c)

The combination of steps (a) and (b) provides an extracted and washed material which is rich in desired polar lipids, but which can still contain undesired components such as monoglycerides, diglycerides, triglycerides, free fatty acids, and astaxanthins. Step (c) thus uses a third solvent system to separate these undesired components from the desired polar lipids by mixing the extracted and washed material from steps (a) and (b) with a third solvent system which partitions the neutral lipids and the polar lipids. Step (c) thus increases the proportion of desired polar lipids relative to the undesired components.

The third solvent system partitions polar lipids and neutral lipids into two or more separable phases. For example the polar lipids and neutral lipids may each be present in a liquid phase, wherein the two phases are separable (e.g. two separate phases in a multi-phase liquid system). As an alternative, the third solvent system may cause a precipitate to form, which may be enriched either for polar lipids or neutral lipids. The two phases (e.g. two liquids, or a solid precipitate and a liquid) are then separated to recover the desired polar lipid component.

Preferably the third solvent system comprises a ketone (e.g. of formula $R^4$—(CO)—$R^5$ where $R^4$ and $R^5$ are any groups other than H, but are preferably independently selected from a $C_1$-$C_6$ alkyl or alkenyl group, an aryl group, or together form a cycloalkyl) or a low molecular weight ester (e.g. $R^6$—(CO)—O—$R^7$ where $R^6$ and $R^7$ are independently selected from a $C_1$-$C_6$ alkyl group). A preferred example of a ketone is acetone. A preferred example of a low molecular weight ester is ethyl acetate. A further but less preferred example of a suitable solvent system is methanol.

Step (c) is carried out by mixing the material arising from steps (a) and (b) with the third solvent system. For instance, acetone or ethyl acetate can be added to the washed lipid-rich phase. In general, the lipid-rich phase is mixed with at least one volume of solvent, and ideally with a volume excess of solvent e.g. using a volume of solvent which is 2-fold to 8-fold the volume of the lipid-rich phase, such as from 2-fold to 5-fold. This mixing can be achieved simply by combining the components, but it is preferable to use active mixing e.g. by stirring, inversion, or other appropriate means. Mixing is typically achieved by stirring, which is preferably carried out at 50 to 500 rpm, or 100 to 200 rpm. Stirring or other active mixing steps may be continued for as long as desired to ensure adequate contact between different components, and this can usually be achieved in an hour or less, although longer periods can also be used.

Preferably step (c) results in precipitation of the desired polar lipids, although it is possible instead that the polar lipids remain in solution and the undesired components are removed as precipitates. For example when acetone or ethyl acetate is used, the polar lipids precipitate and undesired components are present at reduced concentration in the precipitate. On the other hand if methanol is used as the third solvent system then desired polar lipids remain in solution and undesired lipids are precipitated.

A preferred step (c) uses acetone as the third solvent system to precipitate desired polar lipids, and the precipitated material is collected for further use.

Temperature control can be important during step (c). Typically, substantially all of the washed lipid-rich material is dissolved in the third solvent system, for which temperatures of room temperature or above will usually suffice. The temperature is then reduced in order to permit phases to separate. For example, the material can be dissolved in acetone at room temperature, and then the solution can be cooled to cause the desired polar lipids to precipitate. The upper liquid phase (i.e. the acetone with its dissolved undesired components) can then be discarded (e.g. removed by suction), leaving precipitated polar lipids in purer form. Thus the third solvent system is ideally used at two temperatures, where the colder temperature causes precipitation which increases the proportion of desired polar lipids relative to the undesired components. Cooling to below 10° C. e.g. below 5° C., or even below 0° C. is typical.

Addition of the third solvent system can be performed more than once within step (c). Thus a polar lipid-rich composition can be separated from the other components of the mixture, and then mixed again with at least one volume of solvent. For example, where the desired lipid-rich phase is a precipitate, excess solvent can be removed and then the precipitate can be re-dissolved in at least one volume of further solvent, and then re-precipitation can be performed. Dissolution may be achieved by adding further third solvent system to the precipitate, followed by heating to a temperature at which the precipitate re-dissolves (e.g. about 10-25° C., 15-22° C., 18-20° C.). The solution is then re-subjected to conditions at which the polar lipid rich phase precipitates. Overall, precipitation may be carried out from 2-6 (e.g. 3-5 or 4-5) times in order to sequentially increase the purity of desired polar lipids.

The third solvent system displays differential solubilisation of the desired polar lipids compared to neutral lipids. In cold acetone, for instance, phospholipids are generally insoluble whereas various undesired components are soluble e.g. neutral lipids, astaxanthins, and free fatty acids (particularly free unsaturated fatty acids; some free saturated fatty acids may precipitate with phospholipids).

The material that is obtained by this step (e.g. the precipitate after cold acetone precipitation) generally contains at least 90% phospholipid w/w (weight of phospholipids/total weight of lipids in the precipitate) e.g. ≥95%, ≥96%, ≥97%, ≥98%, or even ≥99%. Moreover, and in contrast to the material produced in reference 3, it generally includes low levels of astaxanthins. Furthermore, free fatty acids are typically undetectable (i.e. below the LOQ).

Step (c) provides a composition which is rich in desired polar lipids, but this material will contain residual solvent(s) from the third solvent system (e.g. acetone) and usually includes some residual water. Thus the process ideally includes a further step (d) comprising removal of residual organic solvent component(s) and/or water from the composition.

To remove residual organic solvent components and/or water, two techniques will in general be required: a first which removes organic solvent and one which then removes water but can also remove final residual organic solvent. For example, removal of organic solvent can conveniently be achieved by techniques such as evaporation (e.g. on a rotary evaporator, rather than falling film evaporation due to the solid nature of the material). Water removal can then be achieved by lyophilisation, which can also remove any residual organic solvent (such as acetone). Thus evaporation and freeze drying can be carried out sequentially.

Compared to the material produced after step (c), performing step (d) can provide a lipid-rich composition which has an acetone content of less than about 0.1% by weight e.g. less than 0.01%, or less than 0.005% (see below) and/or less than about 5%, 4%, 3%, 2%, 1%, 0.5% by weight water. This material is suitable for pharmaceutical use.

General Conditions for the Process

As set out above, steps (a) and (b) are performed in either order. Thus the process may comprise steps (a)-(b)-(c) or steps (b)-(a)-(c). Preferably the process comprises steps (a)-(b)-(c) in that order.

Unless specified otherwise herein steps (a) to (c) of the process are generally performed at room temperature (e.g. at between 10-25° C., such as between 15-22° C., or about 18-20° C.), but as noted above that step (c) will usually be performed at lower temperatures as noted above and step (b) may also be performed at lower temperatures. Although the temperature during any step may be controlled, it is not essential that it remains constant during the step. Nevertheless, the temperature during any step is preferably controlled such that the temperature does not deviate more than ±2.5° C. for at least half of the total duration of that step. Ideally, the temperature from starting step (a) to completing step (c) (and completing step (d), if it is performed) does not rise above 50° C.

The process is in general carried out at or around atmospheric pressure.

Because the invention aims at polar lipids of pharmaceutical grade, solvents and other materials used during a process of the invention should be of an appropriate quality e.g. pharmacopoeial quality or better. Furthermore, it is preferred to use only pharmaceutically acceptable solvent components which are regarded as safe in humans, so that residual solvent is not a safety risk. ICH topic Q3C defines guidelines for residual solvents, and groups solvents into three classes. Pharmaceutically acceptable organic solvent components used in processes of the invention are thus preferably selected only from Q3C 'class 3' (i.e. acetic acid, heptane, acetone, isobutyl acetate, anisole, isopropyl acetate, 1-butanol, methyl acetate, 2-butanol, 3-methyl-1-butanol, butyl acetate, methylethyl ketone, tert-butylmethyl ether, methylisobutyl ketone, cumene, 2-methyl-1-propanol, dimethyl sulfoxide, pentane, ethanol, 1-pentanol, ethyl acetate, 1-propanol, ethyl ether, 2-propanol, ethyl formate, propyl acetate, and formic acid). Thus solvent components such as chloroform and hexane, whose complete removal is extremely difficult and time-consuming, can be avoided (unlike, for instance, reference 4 which uses hexane, reference 5 whose 'Folch' and clarification techniques use chloroform, and reference 6 which also uses chloroform); dichloromethane is a further solvent which can be avoided. Ideally, the processes use as few organic solvent components as possible e.g. only 2 or 3 organic solvent components in total. Thus a process in which ethanol and acetone are the only 2 organic solvent components is advantageous for preparing a final pharmaceutical product.

Where ethanol is used as a solvent component (e.g. in the first or second solvent system), it is possible to use aqueous ethanol, or absolute ethanol (i.e. ethanol having a water content of <1% by weight). For instance, step (a) can be performed using 99.5%, 99.8% or even 100% ethanol. For cost reasons, however, it is preferred to use aqueous ethanol e.g. 95% ethanol (which usually contains 92.0-92.7% w/w or 94.7-95.2% v/v ethanol). Concentrations will be calculated accordingly, taking water into account. Pharmacopoeial-grade ethanol is widely available.

Where steps (a) to (c) involve separating two components, active mixing should typically cease to allow those components to separate e.g. to allow two liquid phases to separate, or to allow a precipitate to settle.

Preferably at least one of steps (a) to (d) is performed under an atmosphere containing less oxygen than air. Thus a step may be performed under an inert gas e.g. under nitrogen. These conditions can help to reduce peroxidation of PUFAs to form lipid peroxides, which then can polymerise to produce polymerised PUFAs. Preferably, all of steps (a) to (d) are performed under an inert gas.

Similarly, it is preferred to use degassed solvent components (e.g. degassed ethanol). In particular, the amount of dissolved oxygen in the solvent should be less than 150 μl/ml e.g. <50 μl/ml. This can be achieved by various methods e.g. by purging the solvent by bubbling nitrogen or argon through it for at least half an hour, or by atmosphere exchange under sonication.

It is preferred that the process should not be performed under bright light, although darkness is not required. Again, this helps to avoid polymerisation of PUFAs.

Phospholipid Compositions

The invention provides a phospholipid-rich composition obtainable or obtained by any of the processes of the invention e.g. after step (c) or after step (d).

The invention also provides a composition comprising a mixture of phospholipid compounds of formula (I):

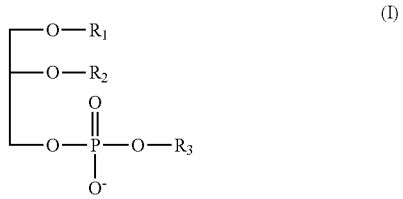

wherein:
- $R_1$ and $R_2$ are each independently selected from a fatty acid moiety of formula $-COC_nH_m$, a fatty acid moiety of formula $-CH_2C_nH_m$, and $-H$;
- $R_1$ and $R_2$ include omega-3 fatty acid moieties, such that at least 30% by weight of the phospholipid compounds is composed of omega-3 fatty acid moieties;
- at least 90% by weight of total omega-3 fatty acid moieties are at position $R_2$;
- $R_1$ and $R_2$ are not both $-H$ in a phospholipid compound, and $R_1$ or $R_2$ is $-H$ in less than 3% by weight of the compounds of formula (I);
- $R_3$ is selected from $-H$, a choline moiety, an ethanolamine moiety, a N-acetylethanolamine moiety, an inositol moiety, and a serine moiety; and
- $R_3$ is a choline moiety in at least 85% by number of the compounds of formula (I).

Typically, and as explained in more detail below, the composition also has one or more of the following properties:
- (a) at least 85% by weight of the composition consists of phospholipid compounds of formula (I). In these embodiments, it is preferred that the composition is substantially free from acetone;
- (b) the weight ratio of C16:0/C14:0 fatty acid moieties in the mixture is between 10:1 and 18:1 and/or the weight ratio of C18:4 n−3/C18:3 n−3 fatty acid moieties is between 1:1 and 3:2;
- (c) the composition includes less than 300 μg astaxanthins per gram of phospholipid;
- (d) the composition comprises less than 0.01% by weight trimethylamine N-oxide
- (e) the composition comprises less than 0.01% by weight homarine;
- (f) the composition includes less than 5% by weight water;
- (g) the composition has less than about 0.03% by weight PUFA polymers
- (h) the mixture includes both phospholipids where $R_1$ is a fatty acid moiety of formula $-COC_nH_m$ and phospholipids where $R_1$ is a fatty acid moiety of formula $-CH_2C_nH_m$;
- (i) the mixture includes both phospholipids where $R_1$ is an omega-3 fatty acid moiety and phospholipids where $R_2$ is an omega-3 fatty acid moiety;
- (j) the composition includes less than 5% by weight sphingomyelin;
- (k) the composition is free from chloroform and hexane; and/or
- (l) less than 0.9% by weight of phospholipids in the composition is formed of compounds where $R_1$ or $R_2$ is $-H$, or more than 1.1% by weight of phospholipids in the composition is formed of compounds where $R_1$ or $R_2$ is $-H$.

The invention also provides a process comprising a step of combining (1) a composition as defined above, having one or more of properties (a) to (l), with (2) a pharmaceutically acceptable carrier, excipient, or diluent.

The invention also provides a composition comprising (1) a solvent and (2) a mixture of phospholipid compounds of formula (I), as defined above, and further having one or more of properties (b) to (l), wherein the phospholipid compounds of formula (I) are dissolved, suspended or emulsified in the solvent, and wherein the composition is liquid at 20° C.

$R_1$ and $R_2$ $R_1$ and $R_2$ are each independently selected from the group consisting of a fatty acid moiety of formula $-COC_nH_m$, a fatty acid moiety of formula $-CH_2C_nH_m$, and $-H$. $R_1$ or $R_2$ is $-H$ in only a small fraction of the compounds of formula (I) i.e. less than 3% by weight of the phospholipid compounds are lysophospholipids (see below). Thus most $R_1$ and $R_2$ are $-COC_nH_m$ or $-CH_2C_nH_m$. Where $R_1$ or $R_2$ has formula $-COC_nH_m$ the fatty acid moiety has an ester linkage, but where $R_1$ or $R_2$ has formula $-CH_2C_nH_m$ the fatty acid moiety has an ether linkage. In these formulae $C_nH_m$ refers to the aliphatic chain which is seen in a naturally-occurring fatty acid (e.g. as seen in krill). For any value of n, m=2n+1 when the fatty acid moiety's aliphatic chain is saturated, but m is reduced by 2 for each unsaturated bond (double bond) in the aliphatic chain i.e. m=2n−1 if one unsaturated bond is present, m=2n−3 if two double bonds are present, m=2n−5 if three double bonds are present, etc. Thus, in general, n is an integer in the range of 4-24 and m=2(n−p)+1, where p is the number of double bonds in the fatty acid moiety. As disclosed in reference 7, the value of n for krill is generally within the range of 11 to 21, and krill phospholipids can include fatty acid moieties with up to six double bonds.

Typically, where a fatty acid moiety at position $R_1$ or $R_2$ is of formula $-CH_2C_nH_m$, the fatty acid moiety is either saturated or monounsaturated. Thus, where $R_1$ or $R_2$ is of formula $-CH_2C_nH_m$, the relationship between n and m is m=2n+1 at that position. In a single molecule, however, it is possible to have a fatty acid moiety of formula $-COC_nH_m$ at one of $R_1$ and $R_2$ (i.e. ester-linked) and a fatty acid moiety of formula $-CH_2C_nH_m$ at the other of $R_1$ and $R_2$ (i.e. ether-linked). Furthermore, usually 90% (molar) or more of the ether-linked fatty acid moieties will generally be C16 and/or C18 (i.e. where n=15 or 17), unsaturated (e.g. C16:0) or monounsaturated (e.g. C18:1), and ether-linked omega-3 fatty acid moieties are generally not present. Overall, within the mixture, it is preferred that no more than 10% by number of the fatty acid moieties are of formula $-CH_2C_nH_m$ (i.e. 10% or fewer of fatty acid moieties are ether-linked, and more than 90% are ester-linked). It is preferred, though, that the phospholipid mixture should include ether-linked fatty acid moieties i.e. they should not be undetectable. Ether-linked fatty acid moieties are readily detected and quantified by NMR (e.g. see reference 7).

In general, $R_1$ and $R_2$ are not both of formula $-CH_2C_nH_m$ in any single phospholipid molecule. Furthermore, fewer than 5% by number (e.g. fewer than 1% by number, or even zero) of the phospholipid molecules in the mixture have $R_2$ of formula $-CH_2C_nH_m$. In other words, ether-linked fatty acid moieties within the mixture may be seen at $R_1$, but not at $R_2$. Thus, in some embodiments: $R_1$ is selected from a fatty acid moiety of formula —$COC_nH_m$, a fatty acid moiety of formula —$CH_2C_nH_m$, and —H; and $R_2$ is selected from a fatty acid moiety of formula —$COC_nH_m$, and —H.

In some embodiments: $R_1$ is selected from a fatty acid moiety of formula —$COC_nH_m$, a fatty acid moiety of formula —$CH_2C_nH_m$ where m=2n+1, and —H; and $R_2$ is selected from a fatty acid moiety of formula —$COC_nH_m$, and —H. Thus, within the mixture: $R_1$ is an ester-linked fatty acid, an ether-linked saturated or monounsaturated fatty acid, or hydrogen; and $R_2$ is either an ester-linked fatty acid moiety or hydrogen; provided that $R_1$ and $R_2$ are not both hydrogen in a single molecule.

The term "fatty acid" refers to a carboxylic acid with an unbranched aliphatic chain, which may be saturated or unsaturated. These have the general formula $C_nH_m$—COOH Long chain polyunsaturated fatty acids (LC-PUFAs) are in general fatty acids that have a n value of 19 or more. Polyunsaturated refers to unsaturation at two or more bonds. The term "fatty alcohol" refers to an alcohol with an unbranched aliphatic chain, which may be saturated or unsaturated, and they have the general formula $C_nH_m$—$CH_2OH$. The term "fatty acid moiety" as used herein refers to the aliphatic chain $C_nH_m$ from such fatty acids and fatty alcohols, and the nature of the moiety can be defined by referring to the corresponding fatty acid and/or fatty alcohol. Thus, for a fatty acid moiety of formula —$COC_nH_m$ or —$CH_2C_nH_m$ the corresponding fatty acid is $C_nH_m$—COOH and the corresponding fatty alcohol has formula $C_nH_m$—$CH_2OH$. By way of example the fatty acid DHA ($C_{21}H_{31}$COOH) corresponds to a fatty acid moiety of formula —$COC_{21}H_{31}$ or —$CH_2C_{21}H_{31}$, and EPA ($C_{19}H_{29}$COOH) corresponds to a fatty acid moiety of formula —$COC_{19}H_{29}$ or —$CH_2C_{19}H_{29}$.

$R_1$ and $R_2$ can thus be fatty acid moieties that contain saturated or unsaturated aliphatic chains, but at least 30% by weight of the phospholipid mixture is composed of omega-3 fatty acid moieties at the $R_1$ and $R_2$ positions (i.e. omega-3 fatty acid moieties provide at least 30 g for every 100 g of phospholipid compounds in the mixture). Omega-3 fatty acids are polyunsaturated fatty acids whose final double bond is positioned between the third and fourth carbon atoms from the methyl end of the hydrocarbon chain. Non-limiting examples of omega-3 fatty acids include 5,8,11,14,17-eicosapentaenoic acid (EPA), 4,7,10,13,16,19-docosahexanoic acid (DHA) and 7,10,13,16,19-docosapentanoic acid (DPA). At least 90% by weight of total omega-3 fatty acid moieties in a phospholipid mixture are at position $R_2$ within formula (I). At least 50% by weight of total omega-3 fatty acid moieties in a phospholipid mixture are EPA and/or DHA (i.e. weight of DHA and EPA/total weight of omega-3 fatty acid moieties in the phospholipids of formula I).

The weight contribution of total omega-3 fatty acid moieties at the $R_1$ and $R_2$ positions can be determined by extracting total phospholipids from the mixture e.g. using the method of reference 8. This is followed by hydrolysis of the lipids to release fatty acids. The released fatty acids are converted to fatty acid esters e.g. fatty acid methyl esters and these esters are analysed e.g. by gas chromatography, HPLC, etc. For instance, the American Oil Chemists' Society has published AOCS Official Method Ce 1b-89 for determining the fatty acid composition of marine oils and marine oil esters by capillary column gas-liquid chromatography. Similarly, reference 7 discloses quantitative analysis of krill oil using HPLC methods based on references 9 and 10 (using evaporative light scattering detection or charged aerosol detection). These established methods provide the amount of specific fatty acids present in a sample, from which the amount of omega-3 fatty acids present in the sample (i.e. in positions $R_1$ and $R_2$ of the phospholipid mixture) can be calculated. In general, references to the content of lipid or phospholipid compositions on a weight/weight basis as referred to herein should be taken as having been determined on the basis of these methods (extraction as in reference 8, followed by processing and analysis by chromatography).

Preferably the phospholipid mixture comprises between 30-40% w/w omega-3 fatty acid moieties.

In some embodiments, the phospholipid mixture comprises both EPA and DHA fatty acid moieties, in which case the EPA and DHA moieties are preferably present in a molar ratio of EPA:DHA of from about 1:1 to about 3:1 (e.g. about 1.5:1 to 2:1, or about 1.8:1 to 2.2:1). The material produced by the process of reference 12 gives a phospholipid mixture having a EPA:DHA ratio of about 1:1 (see Table 2 therein).

Lysophospholipids are formed by hydrolysis of fatty acids from phospholipids, resulting in phospholipids with a single fatty acid moiety. Thus one of $R_1$ or $R_2$ is —H in these lysophospholipid compounds. The invention seeks to avoid high levels of lysophospholipids, and the processes of the invention result in low concentrations of lysophospholipids, namely ≤3% w/w and preferably less than 2%, less than 1%, or even less than 0.5% (weight of lysophospholipid/weight of total phospholipids of formula I). The amount of lysophospholipid may be determined by the HPLC-based analytical methods referred to above, and also by NMR or HP-TLC.

In one embodiment the mixture has a lysophospholipid content of between 1.1-3% w/w, but in other embodiments the mixture has a lysophospholipid content of less than 0.9% w/w. These levels are much lower than see in, for instance, reference 3, where lyso-phosphatidylcholine (LPC) levels were consistently 9% or higher in phospholipids having >50% purity.

$R_1$ and $R_2$ are not both —H in a phospholipid compound. Furthermore, within the composition, it is preferred that molecules of formula (I) where $R_1$ and $R_2$ are both hydrogen are undetectable.

$R_3$ $R_3$ is H or is selected from a choline, ethanolamine, N-acetylethanolamine, inositol and serine. Choline moieties predominate at $R_3$, and the mixture of phospholipid compounds comprises more than 80% choline moieties at position $R_3$ on a molar % basis (mol of choline moieties/total mol phospholipid compounds of formula I), and preferably more than 85% e.g. at least 86, 87, 88, 89, or 90% choline moieties at position $R_3$ on a molar % basis. The mixture of phospholipid compounds can comprise at least 1% (e.g. about 3-15%, 5-12%, 7-10% or 8-9%) ethanolamine and/or N-acetylethanolamine moieties at position $R_3$ on a molar % basis, and preferably a mixture includes at $R_3$ choline and either or both of ethanolamine and/or N-acetylethanolamine. The mixture of phospholipid compounds can comprise <1% of inositol moieties at position $R_3$ on a molar % basis. It is also possible to focus on PE or PC phospholipids, so in some embodiments, the mixture of phospholipids can comprise at least 99% choline at position $R_3$ on a molar % basis; in other embodiments the mixture of phospholipids can comprise at least 99% ethanolamine and/or N-acetylethanolamine moieties at position $R_3$ on a molar % basis. These amounts can be determined for example by using NMR. The methods referred to above can also be used to determine the amounts of these components on a w/w basis (in which the amount of each may be expressed in g/100 g oil).

Within the mixture, for molecules where $R_3$ is a choline moiety, it is preferred that around 5-15% by number of these molecules have an ether-linkage at position $R_1$. Thus, where $R_3$ is choline, 5-15% of these molecules have $R_1$ of formula —$CH_2C_nH_m$, where m=2n+1.

Within the mixture, for molecules where $R_3$ is an ethanolamine or N-acetylethanolamine moiety, it is preferred that around 35-45% by number of these molecules have an ether-linkage at position $R_1$. Thus, where $R_3$ is ethanolamine or N-acetylethanolamine, 35-45% of these molecules have $R_1$ of formula —$CH_2C_nH_m$, where m=2n+1.

Phosphorous-containing groups in phospholipids of the invention may exist in a number of protonated and deprotonated forms depending on the pH of the surrounding environment, for example the pH of the solvent system in which they are dissolved. Therefore, although a particular form may be illustrated in the formula shown above with a negatively-charged $O^-$ group, this is intended to be merely representative and does not limit the invention to a specific protonated or deprotonated form.

Phospholipid Concentration in the Composition

The processes of the invention provide compositions in which polar lipids (e.g. phospholipids when starting from krill material) make up a high proportion of total lipid content. Thus in some embodiments at least 85% by weight of the composition consists of phospholipid compounds of formula (I) e.g. >90%, >95%, >96%, >97%, >98%, or even >99%. The low level of impurities means that such compositions are suitable for pharmaceutical use.

As discussed above, these highly pure compositions can be obtained via the use of acetone precipitation, but it is preferred that the compositions are substantially free from residual acetone. Acetone is classified by ICH guideline Q3C as a class 3 solvent i.e. as having low toxic potential. Recommended intake of such solvents is 50 mg per day or less, and so a composition of the invention ideally has an acetone content of less than about 0.5% by weight e.g. less than 0.1%, or less than 0.01%. Acetone removal is very efficient and can achieve levels as low as 20 mg per kg of purified krill phospholipid (i.e. 0.002% by weight or 20 ppm). Alternatively defined, the composition can be essentially free from acetone.

Although preferred compositions are those in which at least 85% by weight of the composition consists of phospholipid compounds of formula (I), in some embodiments this figure may be reduced, and the invention also contemplates compositions in which at least 75% or 80% by weight of the composition consists of phospholipid compounds of formula (I).

Fatty Acid Signature

The total lipids in wet krill paste (see below) have a relatively high amount of both 14:0 fatty acids (e.g. about 6-10% by weight of total lipids) and a 16:0 fatty acids (e.g. about 15-17% by weight). In contrast, after purification according to the invention the amount of 16:0 fatty acids stays about the same (e.g. 15-17% by weight) whereas the amount of 14:0 fatty acids drops significantly (e.g. to 1.0-1.5% by weight). Thus the ratio of C16:0/C14:0 increases from around 2:1-2.5:1 to about 12:1-16:1, presumably due to the different distribution of fatty acids among neutral lipids compared to polar lipids within krill. Thus a phospholipid mixture of the invention can include both C16:0 and C14:0 fatty acid moieties. The mixture can have a weight ratio of C16:0/C14:0 fatty acid moieties of between 10:1 and 18:1 e.g. between 12:1 and 16:1. This ratio is one distinction between the phospholipid mixtures of the invention and those of references 4 (see in particular Table 5 therein, showing a ratio of about 4.2:1), 11 (see Table 15, with a ratio of about 3.3:1 in Fraction I) and 13 (see Table 2, with a ratio of about 5.3:1 in the polar fraction of krill oil).

The weight ratio of 18:4 n−3 fatty acids to 18:3 n−3 fatty acids in wet krill paste is typically between 2:1 and 3:1. In contrast, after purification according to the invention the ratio is between about 1:1 and 1.5:1. Thus the purification decreases this ratio. Thus a phospholipid mixture of the invention can include both C18:4 n−3 and C18:3 n−3 fatty acid moieties. The mixture can have a weight ratio of C18:4 n−3/C18:3 n−3 fatty acid moieties of between 1:1 and 3:2. The presence of these fatty acid moieties is one distinction between the phospholipid mixtures of the invention and those of reference 4 (see in particular Table 5 therein). A ratio between 1:1 and 3:2 is one distinction between the phospholipid mixtures of the invention and those of references 11 (see Table 15, with a ratio of about 3:1 in Fraction I), 13 (see Table 2, with a ratio of about 3.4:1 in the polar fraction of krill oil), and 12 (see Table 2, with a ratio of about 1.8:1).

Ideally, a composition has both of these properties i.e. a weight ratio of C16:0/C14:0 fatty acid moieties of between 10:1 and 18:1 (e.g. between 12:1 and 16:1) and also a weight ratio of C18:4 n−3/C18:3 n−3 fatty acid moieties of between 1:1 and 3:2.

In some embodiments, a phospholipid mixture of the invention contains <8% oleic acid (molar % of fatty acid moieties which are oleic acid moieties). Much higher levels of oleic acid were seen in, for instance, reference 5 (see FIG. 4C therein).

Astaxanthins

Contrary to the preference in reference 3, where krill phospholipids include 3 g/kg astaxanthins, compositions of the invention ideally include very low levels of astaxanthins (i.e. free astaxanthin and esters thereof) because, despite their advantageous antioxidant properties, the inventors see these compounds as pharmacological impurities which have a biological effect. Processes of the invention have the advantage that they can remove residual astaxanthins from the phospholipids. The composition of the invention can have a concentration of astaxanthins which is less than 300 μg per gram of phospholipid (i.e. less than 0.03% by weight), and preferably less than 0.01% by weight. Processes of the invention can readily reduce astaxanthins to much lower levels and so compositions of the invention can even have less than 0.002% by weight astaxanthins (i.e. <20 mg astaxanthins per kg phospholipids) or less than 0.001%. Astaxanthin content can be measured by HPLC e.g. using UV detection.

Levels of astaxanthins are expressed herein as diol equivalents i.e. as free astaxanthin, without including the weight of any esterification (e.g. to fatty acids).

Astaxanthins can be removed in step (c), and in general this step removes astaxanthin monoesters.

TMAO

In some embodiments the composition comprises less than 0.01% by weight TMAO e.g. 0.005%. Ideally, TMAO is undetectable. TMAO is removed primarily by washing step (b). About 85% of the TMAO can be removed in a single washing step (b), and the inventors have observed that the amount of TMAO present in a krill-derived phospholipid-rich composition is undetectable. TMAO levels can also be expressed relative to the phospholipid compounds. As such the TMAO content can be expressed as a molar ratio such that compositions of the invention have a molar excess of phospholipids to TMAO of at least 1,000.

In addition to having low or no TMAO, compositions of the invention can also have less than 0.005% by weight trimethylamine (TMA) e.g. undetectable TMA.

TMA and TMAO can contribute to an unpleasant smell in a composition, and they can also lead to undesirably high viscosity.

Homarine

Homarine (N-methylpicolinic acid) is a morphogenetically active quaternary ammonium base which occurs in tissues of various marine animals, including krill. In some embodiments the composition comprises less than 0.01% by weight homarine e.g. 0.005%. Ideally, homarine is undetectable. Homarine is removed primarily by washing step (b).

Water Content

Compositions of the invention can have a water content of less than about 10% w/w, and preferably less than about 5, 4, 3, 2, or 1% w/w. Water is optionally removed after formation of the phospholipid-rich composition, as described above. Ideally, a composition of the invention is as dry as possible, so a water content of <2% w/w, such as <1% or even <0.5% is desirable.

PUFA Polymers

As a result of using an inert atmosphere, in some embodiments the composition has low concentration of polymers of polyunsaturated fatty acids. Preferably the composition has less than about 0.03, 0.02, or 0.01% w/w PUFA polymers. Polymer content is measured e.g. by NMR or gel permeation chromatography.

Sphingomyelins

Sphingomyelins are sphingophospholipids found in animal cell membranes. They are based on sphingosine, which is an 18-carbon amino alcohol with an unsaturated hydrocarbon chain, and they usually consist of phosphocholine and ceramide, or a phosphoethanolamine head group. Reference 13 discloses a krill polar lipid extract obtained using hexane and acetone, including 8% sphingomyelins. Compositions of the invention can include less than 5% by weight sphingomyelin, and generally include much less than this (or even zero). Thus a composition of the invention may include less than 1% by wt sphingomyelin e.g. <0.1%, <0.01%, or <0.001%.

Residual Organic Solvents

As mentioned above, when making compositions of the invention it is preferred to use only pharmaceutically acceptable solvent components which are regarded as safe in humans. Pharmaceutically acceptable organic solvents are listed above (Q3C 'class 3'). Thus compositions of the invention are preferably free from organic solvent components which are not in this list e.g. they should be free from chloroform and hexane. If a composition includes a residual organic solvent, this is preferably a 'class 3' solvent, and it is even more preferred that a composition with residual organic solvent should include residues of only 2 or 3 organic solvents in total e.g. residue only of ethanol and acetone.

Omega-6 Fatty Acid Moieties

Omega-6 fatty acids can be inflammatory, so they are ideally kept at low levels in compositions of the invention. Thus in some embodiments of the invention the total amount of omega-6 fatty acids (in particular those contributed by the phospholipid mixture) is less than 2% by weight, and ideally less than 1.5% or even less than 1%. This low level of omega-6 fatty acids is not seen in, for instance, the krill phospholipids purified in reference 4, where Table 5 reports 18% 20:4 n–6 fatty acids and 3.5% 18:2 n–6 fatty acids. Similarly, Table 2 of reference 13 reports 4.4% n–6 fatty acids in the polar fraction of krill oil.

Free Fatty Acids

As mentioned above, the process of the invention can efficiently separate phospholipids from free fatty acids (FFA). In general, compositions of the invention include less than 2% by weight free fatty acids, and ideally less than 1%, preferably less than 0.5%. In general, a high level of FFA may indicate a high level of lysophospholipids.

In contrast, the process described in reference 12 produces phospholipid extracts having high FFA levels (e.g. see page 28 therein reporting at least 4% FFA, and Table 5 reporting at least 5%).

Other Organic Components

Usually, compositions of the invention are free from canthaxanthin (i.e. free canthaxanthin, and esters thereof, are undetectable), unlike those of references 11 (e.g. see Table 18 therein) and 12 (e.g. see Table 5 therein).

Usually, compositions of the invention are free from flavonoids (i.e. flavonoids are undetectable), unlike those of reference 12 (e.g. see Table 5 therein).

Usually, compositions of the invention will include less than 7 IU of vitamin A per gram of phospholipid, and ideally less than 1 IU. When phospholipids of formula I make up more than 95% by weight of a composition of the invention then vitamin A may be present even at less than 0.3 IU per gram of phospholipid. These levels are much lower than reported in reference 3.

Preferred Compositions

With reference to the features mentioned above, a preferred composition which comprises a mixture of phospholipid compounds of formula (I) has properties (a), (c), (d), (h), and (k) as noted above. This composition preferably also has property (f) and/or properties (e) and (j). Thus a composition with all of properties (a), (c), (d), (e), (f), (h), (j), and (k) is particularly preferred.

With reference to property (h), fatty acid moieties of formula —$CH_2C_nC_m$ are either saturated or mono-unsaturated, and not polyunsaturated, such that $m=2n+1$. The value of n is from 11-21.

Usually, the compounds of formula (I) in such compositions will include (1) both C16:0 and C14:0 fatty acid moieties and/or (2) both C18:4 n–3 and C18:3 n–3 fatty acid moieties. Such compositions should also have characteristic (b) as noted above. Preferably the phospholipids include C16:0, C14:0, C18:4 n–3 and C18:3 n–3 fatty acid moieties.

When the composition has property (f), the amount of water is ideally less than 2% by weight.

Further useful properties of these preferred compositions are:

(m) the composition has less than 1% by weight free fatty acids;

(n) the composition has less than 0.005% by weight trimethylamine; and/or (o) the composition is free from canthaxanthin and flavonoid.

Thus one preferred composition has properties (a), (b) (c), (d), (e), (f), (h), (j), (k), (m), (n), and (o), wherein: with reference to property (h) fatty acid moieties of formula —$CH_2C_nC_m$ are either saturated or mono-unsaturated, and not polyunsaturated; the compounds of formula (I) include C16:0, C14:0, C18:4 n–3 and C18:3 n–3 fatty acid moieties; and wherein the amount of water is optionally less than 2% by weight.

In these compositions the phospholipids of formula (I) can include EPA and DHA moieties in a molar ratio (EPA:DHA) of from 1.8:1 to 2.2:1.

Downstream Uses of Phospholipid Compositions

Phospholipid compositions of the invention can be formulated as a pharmaceutical. Thus the invention provides a process for preparing a pharmaceutical composition, comprising: (i) preparing a phospholipid-rich composition from biological material as disclosed above; and (ii) formulating the phospholipid-rich composition as a pharmaceutical.

Step (ii) can take various forms. For instance, the phospholipid-rich composition can be dissolved in a pharmaceutically acceptable organic solvent to form a solution, or it can be dispersed in a pharmaceutically acceptable organic solvent to form a suspension, or it can be combined with a pharmaceutically acceptable aqueous carrier to form an emulsion. These pharmaceutical compositions should be liquid at 20° C. to facilitate administration to patients (e.g. by injection) or to facilitate handling and dosing of the phospholipid mixtures.

The phospholipid-rich composition can be dissolved in a pharmaceutically acceptable solvent, such as ethanol or an aqueous solution of ethanol. The resulting phospholipid solution can comprise about 50-70% (preferably 55-65%) phospholipid and about 30-50% (preferably 35-45%) pharmaceutically acceptable solvent on a w/w basis. The phospholipid solution may then optionally be combined with one or more further pharmaceutically acceptable components e.g. it can be mixed with further components, or it can be filled into a capsule for oral administration.

The phospholipid-rich composition can alternatively be mixed with a pharmaceutically acceptable solvent to form a suspension or an emulsion. The emulsion can be an oil-in-water emulsion or a water-in-oil emulsion.

The phospholipid-rich composition can alternatively be mixed with a solid pharmaceutically acceptable carrier, excipient, or diluent to form a solid pharmaceutical material. The lipid composition can, for instance, be treated by cryogenic grinding (freezer milling) before such mixing.

The invention also provides a pharmaceutical composition comprising a phospholipid-rich composition of the invention in combination with one or more pharmaceutically acceptable carriers, excipients, or diluents. Preferred compositions are liquid at 20° C.

Liquid compositions of the invention can be filled into capsules (e.g. suitable for oral administration), and so the invention also provides a solid capsule which encapsulates a liquid composition which comprises a phospholipid-rich composition of the invention in combination with one or more pharmaceutically acceptable carriers, excipients or diluents.

The invention also provides a phospholipid-rich composition of the invention for use in medicine. Similarly, it provides the use of a phospholipid-rich composition of the invention in the manufacture of a medicament for use in medicine. Similarly, it provides a method for treating a subject in need of a pharmaceutical composition of the invention.

Pharmaceutical compositions of the invention are suitable for various medical uses, particularly in humans. For instance, they can be used to reduce serum triglycerides, reduce serum cholesterol, reduce plaque formation, reduce platelet aggregation, treat atherosclerosis, improve cardiovascular health, reduce inflammation, reduce coronary heart disease, treat depression, treat Alzheimer's disease, treat attention deficit disorder, and treat metabolic syndrome.

They can be used to treat a disease or condition associated with red blood cells and cell membranes, and in particular a disease or conditions associated with an abnormality in red blood cells of cell membranes. In some embodiments, the condition or disease is sickle cell disease, sickle cell anemia, or sickle cell trait. In some embodiments, the condition or disease is thalassemia (alpha-, beta- or delta-), thalassemia in combination with a hemoglobinopathy (Hemoglobin E, Hemoglobin S, or Hemoglobin C), splenomegaly, or membrane abnormalities such as acanthocytes or spur/spike cells, codocytes (target cells), echinocytes (burr cells), elliptocytes and ovalocytes, spherocytes, stomatocytes (mouth cells) and degmacytes ("bite cells").

They can be used to treat or prevent a cardiovascular disorder or metabolic syndrome. In some embodiments, the cardiovascular disorder is selected from atherosclerosis, arteriosclerosis, coronary heart (carotid artery) disease (CHD or CAD), acute coronary syndrome (or ACS), valvular heart disease, aortic and mitral valve disorders, arrhythmia/atrial fibrillation, cardiomyopathy and heart failure, angina pectoris, acute myocardial infarction (or AMI), hypertension, orthostatic hypotension, shock, embolism (pulmonary and venous), endocarditis, diseases of arteries, the aorta and its branches, disorders of the peripheral vascular system (peripheral arterial disease or PAD), Kawasaki disease, congenital heart disease (cardiovascular defects) and stroke (cerebrovascular disease), dyslipidemia, hypertriglyceridemia, hypertension, heart failure, cardiac arrhythmias, low HDL levels, high LDL levels, stable angina, coronary heart disease, acute myocardial infarction, secondary prevention of myocardial infarction, cardiomyopathy, endocarditis, type 2 diabetes, insulin resistance, impaired glucose tolerance, hypercholesterolemia, stroke, hyperlipidemia, hyperlipoproteinemia, chronic kidney disease, intermittent claudication, hyperphosphatemia, omega-3 deficiency, phospholipid deficiency, carotid atherosclerosis, peripheral arterial disease, diabetic nephropathy, hypercholesterolemia in HIV infection, acute coronary syndrome (ACS), non-alcoholic fatty liver disease/non-alcoholic steatohepatitis (NAFLD/NASH), arterial occlusive diseases, cerebral atherosclerosis, arteriosclerosis, cerebrovascular disorders, myocardial ischemia, coagulopathies leading to thrombus formation in a vessel and diabetic autonomic neuropathy.

They can be used to treat, prevent, or improve cognition and/or a cognitive disease, disorder or impairment (memory, concentration, learning (deficit)), or to treat or prevent neurodegenerative disorders. In some embodiments, the cognitive disease, disorder or impairment is selected from Attention Deficit Disorder (ADD), Attention Deficit Hyperactivity Disorder (ADHD), autism/autism spectrum disorder (ASD), (dyslexia, age-associated memory impairment and learning disorders, amnesia, mild cognitive impairment, cognitively impaired non-demented, pre-Alzheimer's disease, Alzheimer's disease, epilepsy, Pick's disease, Huntington's disease, Parkinson disease, Lou Gehrig's disease, pre-dementia syndrome, Lewy body dementia, dentatorubropallidoluysian atrophy, Freidreich's ataxia, multiple system atrophy, types 1, 2, 3, 6, 7 spinocerebellar ataxia, amyotrophic lateral sclerosis, familial spastic paraparesis, spinal muscular atrophy, spinal and bulbar muscular atrophy, age-related cognitive decline, cognitive deterioration, moderate mental impairment, mental deterioration as a result of ageing, conditions that influence the intensity of brain waves and/or brain glucose utilization, stress, anxiety, concentration and attention impairment, mood deterioration, general cognitive and mental wellbeing, neurodevelopmental, neurodegenerative disorders, hormonal disorders, neurological imbalance or any combinations thereof. In a specific embodiment, the cognitive disorder is memory impairment.

They can be used to inhibit, prevent, or treat inflammation or an inflammatory disease. In some embodiments, the inflammation or inflammatory disease is selected from organ transplant rejection; reoxygenation injury resulting from organ transplantation [14] including, but not limited to, transplantation of the following organs: heart, lung, liver and kidney; chronic inflammatory diseases of the joints, including arthritis, rheumatoid arthritis, osteoarthritis and bone diseases associated with increased bone resorption; inflammatory bowel diseases (IBD) such as ileitis, ulcerative colitis (UC), Barrett's syndrome, and Crohn's disease (CD); inflammatory lung diseases such as asthma, acute respiratory distress syndrome (ARDS), and chronic obstructive pulmonary disease (COPD); inflammatory diseases of the eye including corneal dystrophy, trachoma, onchocerciasis, uveitis, sympathetic ophthalmitis and endophthalmitis; chronic inflammatory diseases of the gum, including gingivitis and periodontitis; inflammatory diseases of the kidney including uremic complications, glomerulonephritis and nephrosis; inflammatory diseases of the skin including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, Epilepsy, amyotrophic lateral sclerosis and viral or autoimmune encephalitis, preeclampsia; chronic liver failure, brain and spinal cord trauma, and cancer. The inflammatory disease can also be a systemic inflammation of the body, exemplified by gram-positive or gram negative shock, hemorrhagic or anaphylactic shock, or shock induced by cancer chemotherapy in response to proinflammatory cytokines, e.g., shock associated with proinflammatory cytokines. Such shock can be induced, e.g., by a chemotherapeutic agent that is administered as a treatment for cancer. Other disorders include depression, obesity, allergic diseases, acute cardiovascular events, muscle wasting diseases, and cancer cachexia. Also inflammation that results from surgery and trauma can be treated.

Phospholipid-rich compositions of the invention can also be used as non-active pharmaceutical ingredients in pharmaceutical compositions.

In some embodiments, the phospholipids (e.g. krill phospholipids) are administered in a daily dose of from about 0.1 to about 3 grams.

Biological Materials

The invention is based on work developed for purifying phospholipids from krill material, but the processes of the invention are applicable more broadly and may be used more generally to purify polar lipids of interest from various biological sources which contain those lipids. Thus, for instance, the starting biological material may be an algal, plant, or animal material, with marine animals and marine crustaceans being of particular interest. Suitable marine animal starting materials include, but are not limited to, krill, crabs, Calanus, plankton, eggs, crayfish, shrimp, fish (especially herring), mussels, and marine algaes. The biological starting material can be either fresh or frozen, or can be a material produced from an algal, plant or marine animal biomass such as a meal, powder, hydrolysate, or coagulate (paste). The paste may be a wet paste or a dried paste.

The preferred starting material is a krill material. Any species of krill may be utilized. Species of krill include Antarctic krill (*Euphausia superba*), Pacific krill (*Euphausia pacifica*) and Northern krill (*Meganyctiphanes norvegica*). In addition to *E. superba*, other species are known to live in the Antarctic, one in genus Thysanoessa (*T. macrura*) and six in genus *Euphausia*. These include ice krill (*Euphausia crystallorophias*), *E. frigida*, *E. longirostris*, *E. triacantha* and *E. vallentini*. The preferred krill species is *Euphausia superba*.

As well as the advantages associated with the presence of the omega-3 fatty acids in phospholipid form, the use of krill as a source of such fatty acids has other advantages. Krill is abundant and can be harvested easily. Importantly it is very low in the food chain, which results in a relative lack of pollutants in krill when compared to species that are higher up the food chain.

Rather than starting directly with krill organisms, it is preferred to start with krill which have been processed e.g. as disclosed in any of references 15, 16, or 17. Dry or wet krill pastes can be made, but the preferred starting material is wet krill paste. As already known in the art (e.g. see example 4 of reference 15), such a paste can be obtained e.g. by heat treatment of krill organisms in water, separation of solid and aqueous materials by filtration to provide a krill milk, coagulation by heating, separation by filtration, and then pressing to remove water. A process of the invention can thus include an initial step of obtaining wet krill paste from live krill. Heating krill organisms soon after capture can inactivate their endogenous lipases, which can help to ensure that starting material used with the invention has a low intrinsic level of lysophospholipids, thereby reducing the need to remove these impurities during the process of the invention (whereas freezing or freeze-drying does not inactivate the lipases, and so lysophospholipid levels can be high after storage, particularly in the presence of residual water as this can remain active both in the frozen state and also during thawing). Endogenous lipases are a particular concern if the krill are treated by crushing or squeezing after being caught because this procedure quickly liberates their hepatopancreatic lipases, leading to early generation of lysophospholipids.

The wet krill paste is a protein-lipid mixture. Typically, it includes from about 10% to about 30% Phospholipids on a dry w/w basis, and about 20% to 50% protein on a dry w/w basis, and the phospholipids comprise omega-3 fatty acid residues. The wet krill paste can include a lipid fraction having an omega-3 fatty acid content of from about 10% to about 25% on a dry w/w basis. In some embodiments, the phospholipids include greater than about 90% phosphatidylcholine on a dry w/w basis, and they can include less than about 10% ethanolamine on a dry w/w basis. The wet krill paste can include from about 20% to about 45% triacylglycerol on a dry w/w basis. The wet krill paste can include less than about 1% cholesterol. The paste can include from about 0.01 to about 200 mg/kg naturally-occurring astaxanthins.

Large-Scale Processes

The invention provides a large-scale process for preparing phospholipids from krill material containing those phospholipids, wherein the process provides a composition in which the phospholipids form at least 90% by weight of the composition, and wherein the composition has a mass of at least 1 kg.

The krill phospholipids may make up at least 95% by weight of the composition e.g. ≥96%, ≥97%, ≥98%, or more.

The composition may have a mass of at least 2 kg e.g. from 5-100 kg.

Thus this large-scale process is for the first time suitable, using a single batch run, for preparing krill phospholipids at the kilogram scale.

The large-scale process is ideally based on solvent extraction from a starting krill material. As disclosed herein, it may include extraction in a first solvent system, washing in a second solvent system, and treatment also with a third solvent system. Thus the large-scale process can include steps as disclosed elsewhere herein, in order to provide large amounts of krill phospholipids in a form which is suitable for pharmaceutical use.

Class 3 Solvent Processes

The invention provides a process for preparing phospholipids from krill material containing those phospholipids, wherein the process uses solvent systems to provide a composition in which the phospholipids form at least 90% by weight of the composition, and wherein the solvent systems consist of solvent components selected from the group consisting of acetic acid, heptane, acetone, isobutyl acetate, anisole, isopropyl acetate, 1-butanol, methyl acetate, 2-butanol, 3-methyl-1-butanol, butyl acetate, methylethyl ketone, tert-butylmethyl ether, methylisobutyl ketone, cumene, 2-methyl-1-propanol, dimethyl sulfoxide, pentane, ethanol, 1-pentanol, ethyl acetate, 1-propanol, ethyl ether, 2-propanol, ethyl formate, propyl acetate, formic acid, and water.

The krill phospholipids may make up at least 95% by weight of the composition e.g. ≥96%, ≥97%, ≥98%, or more.

This process is ideally based on solvent extraction from a starting krill material as disclosed herein. Thus it may include extraction in a first solvent system, washing in a second solvent system, and treatment also with a third solvent system, but in all cases the components of the solvent systems are selected only from acetic acid, heptane, acetone, isobutyl acetate, anisole, isopropyl acetate, 1-butanol, methyl acetate, 2-butanol, 3-methyl-1-butanol, butyl acetate, methylethyl ketone, tert-butylmethyl ether, methylisobutyl ketone, cumene, 2-methyl-1-propanol, dimethyl sulfoxide, pentane, ethanol, 1-pentanol, ethyl acetate, 1-propanol, ethyl ether, 2-propanol, ethyl formate, propyl acetate, formic acid, and water. Thus pure krill phospholipids can be obtained while avoiding solvent components such as chloroform and hexane.

Ideally, the processes use as few organic solvent components as possible e.g. only 2 or 3 organic solvent components in total. Thus a process in which ethanol and acetone are the only 2 organic solvent components is advantageous for preparing a final pharmaceutical product. Overall, therefore, a process of the invention can use ethanol, acetone, and water as the only solvent components.

MODES FOR CARRYING OUT THE INVENTION

Example 1

This example describes the extraction of oil from a wet material. A coagulum from krill comprising about 70% water, 15% lipids and about 15% other dry matter, mainly proteins, was obtained as described in reference 16. This material was subjected to an extraction procedure as follows. 3500 grams of pure ethanol was added to 1004 grams of the coagulum and stirred for 45 minutes. The mixture was then filtered through a filter paper applying vacuum on the receiving flask to obtain 3854 gram of filtrate. 1179 gram of the filtrate was subjected to evaporation on a rotary evaporator and the obtained dry matter was washed 4 times with a 60% solution of ethanol and finally the solvent was evaporated in a rotary evaporator. The obtained oil, 23.7 gram, was solid at room temperature and comprised 76.8% phospholipids. Water is removed by freeze drying.

The content of EPA was 200 mg/gram and the content of DHA 87 mg/gram oil. The composition of the phospholipid fraction was as follows:

| Phospholipid | Weight-% | Mol-% | MW [g/mol] |
| --- | --- | --- | --- |
| PC | 71.97 | 93.03 | 790.0 |
| 1-LPC | 0.24 | 0.45 | 534.5 |
| 2-LPC | 0.73 | 1.39 | 534.5 |
| PI | —*) | —*) | 907.0 |
| LPI | —*) | —*) | 629.5 |
| PS-Na | —*) | —*) | 833.0 |
| LPS | —*) | —*) | 555.5 |
| SPH | —*) | —*) | 812.0 |
| PE | 3.37 | 4.47 | 770.0 |
| LPE | —*) | —*) | 492.5 |
| APE | —*) | —*) | 1032.0 |
| PG | —*) | —*) | 820.0 |
| DPG | —*) | —*) | 774.0 |
| PA | —*) | —*) | 746.0 |
| LPA | —*) | —*) | 468.5 |
| Other | 0.53 | 0.66 | 812.0 |
| Sum | 76.83 | 100.00 | |
| Phosphorus | 3.03 | | |

Example 2

This example describes an alternative method for extraction of oil from the krill wet material, starting from a frozen paste from krill, which was subjected to an extraction procedure as described below. Unlike example 1, all steps were performed under a nitrogen atmosphere.

The paste comprises about 65% water (assessed via dry matter), 17% lipids (about equal weights of phospholipids and neutral lipids), and about 18% other dry matter, mainly proteins. Within the lipids, the proportions of certain fatty acids by weight were as follows: C16:0 about 15-17%; C14:0 about 6-10%; C18:3 n–3 about 1.4-3.1%; and C18:4 n–3 about 3.5-7%.

100 kg of the frozen coagulum (−20° C.) was added to a vessel. Based on the water content of the coagulum, 350 kg of pure ethanol (99.8% w/w, room temp) was then added to the vessel, giving a final ethanol concentration in the liquid phase of about 84% w/w (~350 kg ethanol in 415 kg liquid solvents). Ethanol was added to give near to the desired final concentration, and then water content was checked by Karl Fischer titration and extra ethanol was added to give the correct final amount.

The mixture was stirred in the vessel for 45 minutes, with gentle heating if required. Four final temperatures were studied in separate batches, namely a) 2° C., b) 10° C., c) 15° C. and d) 20° C. After stirring was complete, the mixtures were allowed to settle, and they each included a red-coloured liquid phase and a wet slurry which contained shell fragments and other insoluble materials. To remove the liquid phase from the slurry the mixtures were decanted, and the liquid material was put through a coarse filter and then serial-filtered through a 75 μm and 5 μm cartridge filter to obtain a) 345 kg, b) 366 kg, c) 372 kg or d) 374 kg of filtrate, with residual material remaining in the filtration cake. Smaller cartridge filters (e.g. 1.2 μm) have also been used.

The filtrates were then subjected to a sequence of washes. Firstly, de-ionized water was added to give ~60% w/w ethanol solutions (a: 137 kg water; b: 149 kg; c: 152 kg; d: 155 kg) and the mixtures were stirred for 10-15 minutes and left to settle for 12-24 h at room temperature (15-20° C.) in vessels having a valve at the base. The bottom phase was isolated by draining the bottom phase through the valve, to give between 5.4-9.0 kg of a lipid-rich fraction. The lipid-rich fraction was re-washed 2 to 5 times with 60% w/w ethanol at room temperature to give a final material which contained about 80% by weight phospholipids and 20% neutral lipids. In even the first wash, 85% of TMAO was removed, and the further washes led to material with undetectable TMAO (less than 1 mgN/100 g i.e. at least 20-fold lower than reported in Table X of reference 18).

This lipid-rich material was treated at least once by cold acetone precipitation. Three parts w/w acetone were added and the lipid rich material was dissolved by gentle heating and slow stirring. The stirring was stopped and the mixture was cooled to 4° C. for precipitation. When the precipitation was complete, the upper solvent phase was removed. This cold precipitation procedure was performed three times in total, after first re-dissolving in fresh acetone each time.

The precipitate was then subjected to evaporation and freeze-drying to remove residual acetone and water. Batch c (i.e. extracted at 15° C., then washed 3×60% EtOH before cold acetone precipitation) provided 1.9 kg of solid material (an orange wax) consisting of 98% phospholipids/1.7% neutral lipids with a water content of 3%. The content of EPA was 19.2 g/100 g and the content of DHA was 11.0 g/100 g solid material. The composition of the phospholipid fraction measured by $^{31}$P NMR was as follows:

| Phospholipid | Weight-% | Mol-% | MW [g/mol] |
|---|---|---|---|
| PC | 82.59 | 89.03 | 790.0 |
| 1-LPC | —*) | —*) | 534.5 |
| 2-LPC | 0.12 | 0.19 | 534.5 |
| PI | 0.47 | 0.44 | 907.0 |
| LPI | —*) | —*) | 629.5 |
| PS-Na | —*) | —*) | 833.0 |
| LPS | —*) | —*) | 555.5 |
| SPH | —*) | —*) | 812.0 |
| PE | 8.25 | 9.13 | 770.0 |
| LPE | —*) | —*) | 492.5 |
| APE | 0.59 | 0.49 | 1032.0 |
| PG | —*) | —*) | 820.0 |
| DPG | —*) | —*) | 774.0 |
| PA | —*) | —*) | 746.0 |
| LPA | —*) | —*) | 468.5 |
| Other | 0.69 | 0.73 | 812.0 |
| Sum | 92.72 | 100.00 | |
| Phosphorus | 3.64 | | |

*)= not observed, no signal assignment

Thus, based on total weight of the material analysed by NMR, nearly 93% of the final material was phospholipid. After compensating for residual water (about 3%), residual organic solvent, and salts/minerals present after ignition, the overall purity was 98%. Thus this process provides phospholipids with higher purity than seen using Example 1.

Further analysis of lipid composition was performed by HPLC, and results are shown below (grams per 100 g of oil):

| Parameter | Results |
|---|---|
| Lipid composition[1] | |
| Triacylglycerol | <0.5 |
| Diacylglycerol | <0.5 |
| Monoacylglycerol | <1 |
| Free fatty acids | <0.5 |
| Cholesterol | <0.5 |
| Cholesterol ester | <0.5 |
| Phosphatidylethanolamine | 7.7 |
| Phosphatidylinositol | <1 |
| Phosphatidylserine | <1 |
| Phosphatidylcholine | 92 |
| Lyso-phosphatidylcholine | <0.5 |
| Total polar lipids | 99.4 |
| Total neutral lipids | <0.5 |
| Total sum lipids | 99.6 |
| Fatty acid composition[2] | |
| Sum saturated fatty acids | 17.8 |
| Sum monoenic fatty acids | 9.1 |
| Sum PUFA (n-6) fatty acids | 1.2 |
| Sum PUFA (n-3) fatty acids | 34.4 |
| Sum total PUFA fatty acids | 35.8 |
| Sum fatty acids total | 62.7 |
| Cholesterol | 0.31 weight % |
| Astaxanthin/esters | <2 mg/kg |
| Water content | 3% |

[1]Calculated based on techniques in refs. 7, 9 & 10.
[2]Calculated as fatty acid methyl esters, by AOCS Ce 1b-89.

Looking at specific fatty acids, proportions were as follows, measured across several batches:

| | C14:0 | C16:0 | 16/14 Ratio | C18:3 n-3 | C18:4 n-3 | 18:4/ 18:3 Ratio |
|---|---|---|---|---|---|---|
| Wet paste | 6-10% | 15-17% | 2-2.5 | 1.4-3.1% | 3.5-7% | 2-3 |
| Final material | 1.0-1.5% | 15-17% | 12-16 | 1.0-2.5% | 1.0-2.5% | 1-1.5 |

The purified phospholipids included both ether-linked and ester-linked fatty acids, but 10% or fewer were ether-linked. NMR showed ether-linked fatty acid moieties at position sn1 but not at sn2, and ether-linked fatty acids were either fully saturated or were monounsaturated. Where a phospholipid was a phosphatidylcholine, about 10% of the molecules included ether-linked fatty acids; where a phospholipid was a phosphatidylethanolamine (with or without N-acetylation), about 40% of the molecules included ether-linked fatty acids. PUFAs were seen only with ester linkages. 30-40% by weight of fatty acids in the purified phospholipids were omega-3, and these were distributed at the sn1 and sn2 positions (mainly at sn2). Most of the omega-3 fatty acids were EPA and/or DHA, with about 2× more EPA than DHA.

The phosphatidylethanolamine content using this process was higher than seen when using the method of Example 1 (about 2× higher).

The lysophosphatidylcholine content (0.2-0.4 mol %) is very low in the purified phospholipids, when compared both to the amount observed using the method of Example 1 (about 1%) and in the starting wet material (about 1.2-1.4 mol %). No molecules were detected where fatty acid chains had been lost at both the sn1 and sn2 positions. Lyso-phosphatidylethanolamine (with or without N-acetylation) and lyso-phosphatidylinositol also were not seen.

Levels of astaxanthins were much lower in the purified phospholipids when compared to the material obtained in Example 1. This reduction was even visible due to the weaker red colour.

Amino acids, TMAO and homarine were all below LOQ by standard analytical methods.

Thus very pure krill phospholipids can be achieved by a process using extraction in 84% ethanol, followed by washing in 60% ethanol, and then multiple steps of cold-acetone precipitation.

Example 3

Rather than being subjected to cold acetone precipitation, the washed lipid-rich material produced during example 2 (80% phospholipid, 20% neutral lipid) was precipitated using ethyl acetate. In initial testing, the material was thoroughly mixed with 3 parts of ethyl acetate at room temperature and then placed at 4° C., −11° C. or −20° C. No precipitation was seen at 4° C., but there was some phase separation at −11° C. and precipitation was observed at −20° C.

Further washed lipid-rich material was mixed with 2, 3 or 5 parts of ethyl acetate and placed at −20° C. to achieve precipitation. With 3 parts of solvent the phospholipid yield was 32%, but with 5 parts of solvent the yield was 66%. Re-precipitation of this material gave results as follows:

| Precipitation | Yield | Phospholipid | Neutral lipid | Phospholipid yield |
|---|---|---|---|---|
| 1 | 65.6% | 96.1% | 3.9% | 81.6% |
| 2 | 95.4% | 99% | 1% | 62.6% |

Thus phospholipids can be effectively purified from the washed krill extract using repeated steps of precipitation with 5 volumes of EtOAc at −20° C.

PUFA Polymerisation

Purified krill phospholipids were exposed to air at 70° C. to investigate polymerisation of PUFAs. After 12 hours of treatment the region in a $^{31}$P NMR spectrum at −0.95 to −1.15 ppm showed a peak with a shoulder to the right. At samples taken during the treatment the peak was higher and the shoulder was less prominent, and in the starting material the peak was sharp with no shoulder. In all cases, however, the integrated area of this spectral region was constant. The shoulder is a pseudomarker of polymerization, either inter- or intra-molecular, and thus represents the conversion of PUFA chains (the main peak) into various polymers. The absence of oxygen during processing of the krill material (e.g. by performing the process under nitrogen) means that this oxidative polymerisation does not occur.

It will be understood that the invention is described above by way of example only and modifications may be made while remaining within the scope and spirit of the invention.

REFERENCES

[1] Batetta et al. (2009) *J Nutr* 139:1495-1501
[2] Di Marzo et al. (2008) *Int Dairy J* 20:231-235
[3] WO 2011/050474
[4] Ali Nehari & Chun (2012) *Korean J Chem Eng* 29(7): 918-24.
[5] Giglotti et al. (2011) *Food Chemistry* 125:1028-36.
[6] US 2013/0310339.
[7] Winther et al. (2011) *Lipids* 46:25-36.
[8] Bligh & Dyer (1959) *Can. J. Biochem. Physiol.* 37:911-917.
[9] Homan R et al. 1998 *J Chromatogr B Biomed Sci Appl* 708:21-26
[10] Moreau et al. 2006 *Lipids* 41:727-734
[11] WO 00/23546.
[12] WO 03/011873.
[13] Watanabe et al. (1991) *Nippon Suisan Gakkaishi* 57:681-94.
[14] Grupp et al. (1999) *J. Mol. Cell. Cardiol.* 31: 297-303.
[15] WO 2009/027692.
[16] WO 2008/117062.
[17] WO 2010/097701.
[18] WO 2013/102792.

The invention claimed is:
1. A composition comprising a mixture of phospholipid compounds of formula (I):

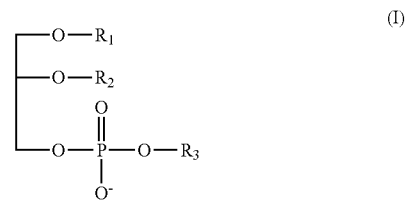

wherein:
$R_1$ and $R_2$ are each independently selected from a fatty acid moiety and —H;
$R_1$ and $R_2$ include omega-3 fatty acid moieties, such that at least 30% by weight of the phospholipid compounds is composed of omega-3 fatty acid moieties;
at least 90% by weight of total omega-3 fatty acid moieties are at position $R_2$;
$R_1$ and $R_2$ are not both —H in a phospholipid compound, and $R_1$ or $R_2$ is —H in less than 3% by weight of the compounds of formula (I);
$R_3$ is selected from —H, a choline moiety, an ethanolamine moiety, a N-acetylethanolamine, an inositol, and a serine; and —$R_3$ is a choline in at least 85% by number of the compounds of formula (I) and wherein the composition has the following properties: (a) at least 85% by weight of the composition consists of phospholipid compounds of formula (I), (b) the composition includes less than 300 pg astaxanthins per gram of phospholipid; (c) the composition comprises less than 0.01% by weight trimethylamine N-oxide; (d) the composition comprises less than 0.01% by weight homarine; (e) the composition has less than about 0.03% by weight PUFA (polyunsaturated fatty acid) polymers (f) the composition includes less than 5% by weight sphingomyelin.
2. The composition of claim 1, wherein less than 0.9% by weight of phospholipids in the composition is formed of compounds where $R_1$ or $R_2$ is —H.
3. The composition of claim 1, further having the following properties:
(g) the mixture includes both phospholipids where $R_1$ is a fatty acid moiety of formula —$COC_nH_m$ and phospholipids where $R_1$ is a fatty acid moiety of formula —$CH_2C_nH_m$;
(h) the mixture includes both phospholipids where $R_1$ is an omega-3 fatty acid moiety and phospholipids where $R_2$ is an omega-3 fatty acid moiety.
4. The composition of claim 3, further comprising: (h) the weight ratio of C16:0/C14:0 fatty acid moieties in the mixture is between 10:1 and 18:1 and/or the weight ratio of C18:4 n−3/C18:3 n−3 fatty acid moieties is between 1:1 and 3:2.

5. The composition of claim 4, further comprising: (i) less than 5% by weight water; (j) the mixture includes both phospholipids where $R_1$ is a fatty acid moiety of formula —$COC_nHm$ and phospholipids where $R_1$ is a fatty acid moiety of formula —$CH_2C_nHm$; and (k) less than 0.9% by weight of phospholipids in the composition is formed of compounds where $R_1$ or $R_2$ is —H, or more than 1.1% by weight of phospholipids in the composition is formed of compounds where $R_1$ or $R_2$ is —H.

6. The composition of claim 5, wherein: the (j) fatty acid moieties of formula —$CH_2C_nCm$ are either saturated or mono-unsaturated, and not polyunsaturated; the compounds of formula (I) include C16:0, C14:0, C18:4 n-3 and C18:3 n-3 fatty acid moieties at $R_1$ and/or $R_2$; the amount of water is less than 2% by weight; the composition has less than 1% by weight free fatty adds; the composition has less than 0.005% by weight trimethylamine; the composition is free from canthaxanthin and flavonoid; and wherein the phospholipids of formula (I) include EPA and DHA moieties in a molar ratio (EPA:DHA) from 1.8:1 to 2.2:1.

7. A composition comprising (1) a pharmaceutically-acceptable solvent and (2) a mixture of phospholipid compounds of formula (I), as defined in claim 1, wherein the phospholipid compounds of formula (I) are dissolved, suspended or emulsified in the pharmaceutically-acceptable solvent, and wherein the composition is liquid when at 20° C.

* * * * *